US006420547B1

(12) United States Patent
Maiti et al.

(10) Patent No.: US 6,420,547 B1
(45) Date of Patent: Jul. 16, 2002

(54) USE OF THE FULL LENGTH TRANSCRIPT (FLT) FROM MIRABILIS MOSAIC CAULIMOVIRUS TO EXPRESS CHIMERIC GENES IN PLANTS

(75) Inventors: Indu B. Maiti; Nrisingha Dey, both of Lexington, KY (US); Robert J. Shepherd, Portland, OR (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 09/324,803

(22) Filed: Jun. 3, 1999

(51) Int. Cl.$^7$ ............................................... C07H 21/04
(52) U.S. Cl. .................... 536/24.1; 435/320.1
(58) Field of Search ............................. 435/320.1, 410, 435/468; 536/24.1; 800/295, 298

(56) References Cited

U.S. PATENT DOCUMENTS 5,850,019 A 12/1998 Maiti et al. .............. 800/317.3

OTHER PUBLICATIONS

Maiti et al., "Gene expression regulated by gene VI of caulimovirus: transactivation of downstream genes of transcripts by gene VI of peanut chlorotic streak virus in transgenic tobacco," Virus Res., 57(2): 113–24 (Oct. 1998) (Maiti I).
Maiti et al., "Isolation and expression analysis of peanut chlorotic streak caulimovirus (PC1SV) full–length transcript (FLt) promoter in transgenic plants," Biochem. Biophys, Res. Commun., 244(2): 440–4 (Mar. 1998) (Maiti II).
Maiti et al., "Promoter/leader deletion analysis and plant expression vectors with the figwort mosaic virus (FMV) full length transcrip (FLt) promoter containing single or double enhancer domains," Transgenic Res., 6(2): 143–56, (1997) (Maiti III).
Mushegian et al., "Genetic elements of plant viruses as tools for genetic engineering," Microbiol. Rev., 59(4): 548–78 (1995) (Mushegian).
Gowda et al (1988) J. Cell Biochem Suppl. 0(12 Part C):296.*

* cited by examiner

Primary Examiner—Robert A. Schwartzman
Assistant Examiner—Bronwen M. Loeb
(74) Attorney, Agent, or Firm—McDermott, Will & Emery

(57) ABSTRACT

A full-length transcript promoter from mirabilis mosaic caulimovirus (MMV) is identified and its DNA sequence given. The promoter functions as a strong and uniform promoter for chimeric genes inserted into plant cells. This strong promoter function is exhibited by histochemical assay in seeds and floral organs and by reproductive scores of transgenic plants including the promoter. The promoter preferably includes a 3' untranslated region that may be from the MMV itself or from a heterologous source with respect to the promoter. The promoter is used in a chimeric gene and in methods for transforming plant cells to obtain transgenic plants, plant tissues, plant cells and seeds incorporating the MMV promoter. The MMV FLT promoter shows greater activity (14 to 24 fold) than the CaMV 35S promoter. A modified MMV FLt promoter with duplicated enhancer domains shows greater activity (3 fold) than with a single enhancer domain.

4 Claims, 11 Drawing Sheets

(2 of 11 Drawing Sheet(s) Filed in Color)

```
-457                                                          -418
 ↓                                   3a      ↓       3b
TGGAGATTCA GAAAAATCTC CATCAACAAA TAATCCAAGT AAGGATTAAT GGATTGATCA  - 398
            -378     2a                         1a         1b   -340
              ↓                                                   ↓
ACATCCTTAC CGCTATGGGT AAGATTGATG AAAAGTCAAA AA CAAAAATC AATTATGCAC  - 338
2b                                 4a -297  4b
 6a      7a       6b        7b                    ↓
ACCAGCATGT GTTGATCACC AGCTATTGTG GGACACCAAT TTCGTCCACA GACATCAACA  - 278
5a                                      5b       8a        9a  9b
                        -248
           10a           ↓        10b
TCTTATCGTC CTTTGAAGAT AAGATAATAA TGTTGAAGAT AAGAGTGGGA GCCACCACTA  - 218
8b          11a 11b -193                 11c
                        ↓                                    14a
AAACATTGCT TTGTCAAAAG CTAAAAAAGA TGATGCCCGA CAGCCACTTG TGTGAAGCAT  - 158
                        -133 12a,12b(as-2)                13a
                        ↓        14b
GTGAAGCCGG TCCCTCCACT AAGAAAATTA GTGAAGCATC TTCCAGTGGT CCCTCCACTC  - 98
  13b       15a  -78              13c                       15b
                  ↓
ACAGCTCAAT CAGTGAGCAA CAGGACGAAG GAAATGACGT AAGCCATGAC GTCTAATCCC  - 38
  16                              as-1       as-1          ↑
                                  TSS(+1)                  -38
                                    ↓             20a
ACAAGAATTT CCTTATATAA GGAACACAAA TCAGAAGGAA GAGATCAATC GAAATCAAAA  + 23
            TATA-box              ↑                 19a
                                 +2
     20b           20c
TCGG AATCGA AATCAAAATC GGAATCGAAA TCTCTCATCT CTCTCTACCT TCTCTCTAAA + 83
     ↑19b                          ↑
     +33                          +63

AAACACTTAG ATGTGTGAGT AATCACCCAC TTGGGGTTGT AATATGTAGT AGTAAATAAG + 143
                                             ↑
                                            +133

GGAACCTTAG GGTATACCAT TGTTGTAATA TTATTTTCAG TATCAATAAA ATAATCTTTC + 203
                                                polyA signal

AGTTTATCTT ATATTCATTT GTGTGACACC GTATTCCCAT AAAACCGATC CTAATCTCTCC + 263
```

FIG.1

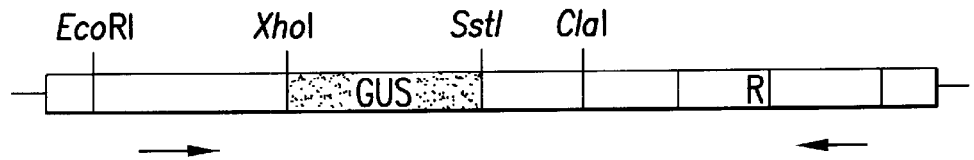
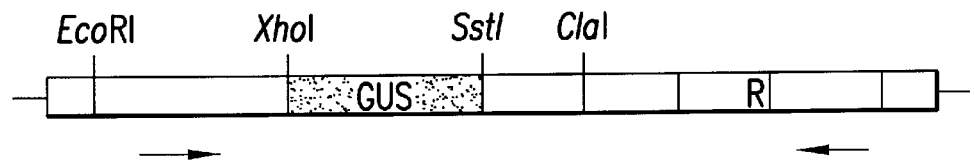
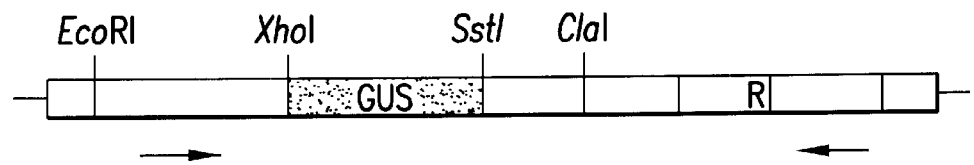
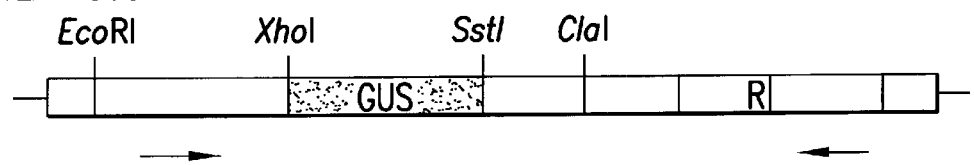
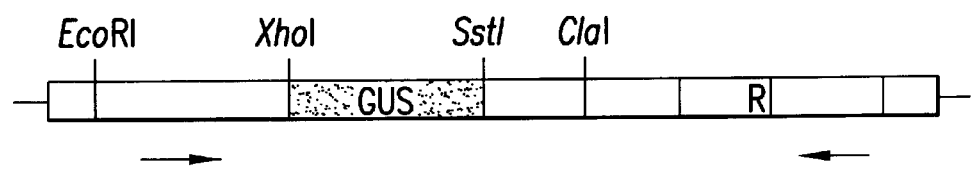
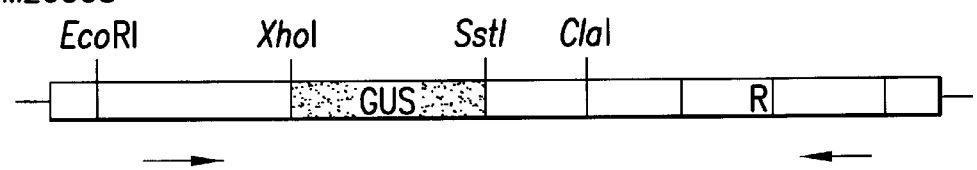
FIG. 6

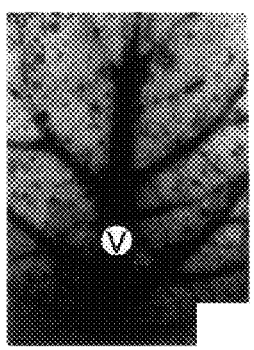 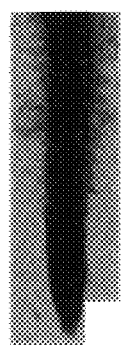 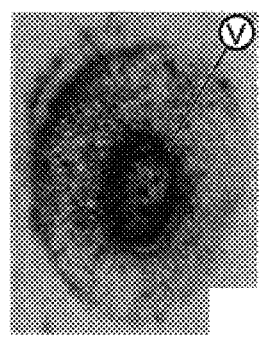 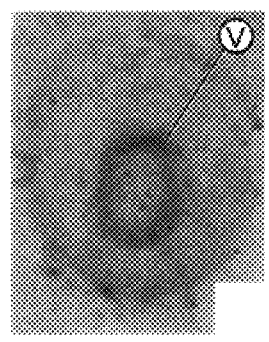
FIG.9A  FIG.9B  FIG.9C  FIG.9D
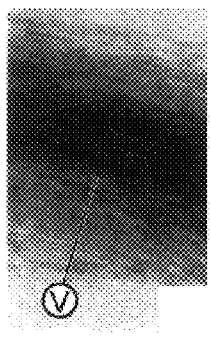 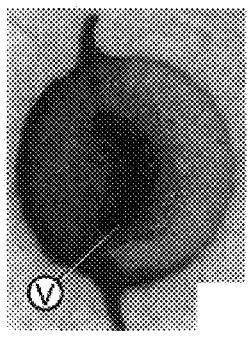 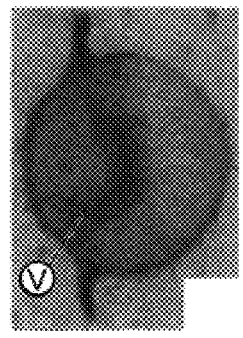 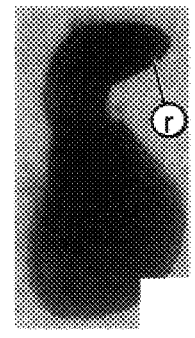
FIG.9E  FIG.9F  FIG.9G  FIG.9H
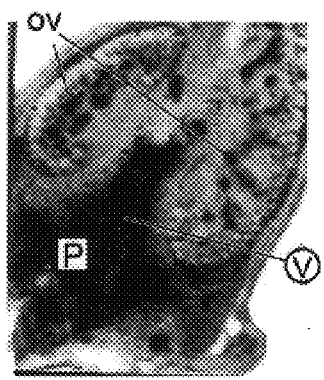 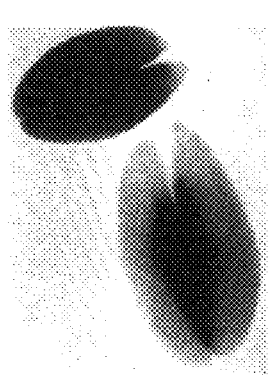 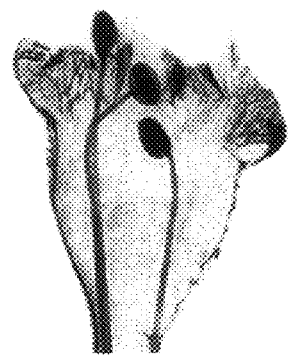
FIG.9I  FIG.9J  FIG.9K

USE OF THE FULL LENGTH TRANSCRIPT (FLT) FROM MIRABILIS MOSAIC CAULIMOVIRUS TO EXPRESS CHIMERIC GENES IN PLANTS

TECHNICAL FIELD

The present invention generally relates to a full length transcript promoter (FLt) sequence from mirabilis mosaic caulimovirus (MMV) and the use thereof to express chimeric genes in plant cells and plants. More particularly, the present invention relates to the use of wild type and modified MMV FLt DNA sequences, or multiple enhancer domains of the MMV FLt DNA sequences, to provide strong promoter activity to direct foreign gene expression in transgenic plants; a chimeric gene construct containing the MMV FLt DNA sequence (or multiple enhancer domains of the MMV FLt DNA sequence) and a coding sequence for a protein of interest; an expression vector containing the chimeric gene construct; a plant cell transformed with the chimeric gene construct; a plant seed transformed with the chimeric gene construct; a plant tissue transformed with the chimeric gene construct; and a transgenic plant transformed with the chimeric gene construct.

BACKGROUND ART

The Caulimoviruses and their Promoters for Plant Genetic Engineering

For plant genetic engineering applications, a number of strong, constitutive promoters have been derived from the genome of two pararetrovirus subgroups namely caulimovirus (Odell et al., 1985; Hasegawa et al., 1989; Sanger et al., 1990; Verdaguer et al., 1996; Maiti et al., 1997; Maiti and Shepherd, 1998) and badnavirus (Medberry et al., 1992; Bhattacharyya-Pakrassi et al., 1993). The caulimoviruses are a group of small circular DNA virus of approximately 8 kb pairs containing 6 to 8 open reading frames (ORFs). The cauliflower mosaic virus (CaMV) is one of the best characterized members of this group. Generally, two major transcript promoters are present in the caulimovirus genome: one is the pregenomic full-length transcript (similar to CaMV 35S transcript), which encompasses the whole genome and the other is the subgenomic transcript (similar to CaMV 19S transcript), which spans only gene VI region of caulimovirus. (Odell et al., 1981; Hasegawa et al., 1989; Driesen et al., 1993). In infected plants, the full-length transcripts (FLts) function both as mRNAs for synthesis of viral proteins and as templates during reverse-transcriptase mediated replication of viral genome (Guilley et al., 1982; Hull and Covey, 1983; Pfeiffer and Hohn, 1983). Transcriptional activity of the CaMV 35S promoter is the result of the combinatorial and synergistic interaction of different cis-elements present in the promoter sequence and the transacting nuclear binding protein factors (Benfey and Chua, 1990; Benfey et al., 1990a; 1990b; Fang et al., 1989).

The CaMV 35S promoter is a well-characterized strong constitutive promoter (Fang et al., 1989; Odell et al., 1985; Ow et al., 1987; Benfey et al., 1989, 1990; 1990a; 1990b; Lam, 1994) that has been extensively used for expressing foreign genes in monocotyledonous and dicotyledonous plants (Holtrof et al., 1995; Mitsuhara et al., 1996; Wilmink et al., 1995). The 35S promoter from CaMV is also active in microbes (Assaad and Singer, 1990; Pobjecky et al., 1990) and in animal cells (Zahm et al., 1989; Ballas et al., 1989).

It has been found that single or multiple copies of enhancer sequences from the CaMV 35S promoter can increase homologous and heterologous promoter expression in an orientation-independent manner (Ow et al., 1987; Kay et al., 1987; Omirulleh et al., 1993). Similar observation was made when single or multiple copies of the enhancer sequence are inserted upstream of the TATA-box of the CaMV 19S promoter (Ow et al., 1987; Driesen et al., 1993), rbcS-3A promoter (Fang et al., 1989) and the nos promoter (Odell et al., 1985). The duplication of enhancer sequences of FMV FLt-promoter (Maiti et al., 1997) and PC1SV-FLt-promoter (Maiti and Shepherd, 1998) also increase promoter activity.

Badnavirus, a subgroup of pararetrovirus, infects only monocotyledonous plants whereas caulimovirus infects dicotyledonous plants. Promoters from badnavirus like Commelana yellow mottle virus (CYMV) and rice tungro bacilliform virus (RTBV) are reported to be primarily active in vascular tissue (Bhattacharyya-Pakrasi et al., 1993; Medberry et al., 1992; Yin and Beachy, 1995).

The genomes of several caulimoviruses including CaMV (Gardner et al., 1981), carnation etched ring virus (CERV), (Hull et al., 1986), figwort mosaic virus (FMV), (Richins, 1987), soybean chlorotic mottle virus (SoCMV), (Hasegawa et al., 1989), peanut chlorotic streak virus (PC1SV), (Richins, 1993), cassava vein mosaic virus (CVMV), (Calvert et al., 1995), strawberry vein banding virus (SVBV), (Petrzik, 1996), and petunia vein clearing virus (PVCV), (Richert-Poggler and Shepherd, 1997) have been fully sequenced.

A number of transcriptional promoters have been derived from the genomes of pararetroviruses: for example the rice tungro bacilliform virus (RTBV), (Bhattacharyya-Pakrasi et al., 1993), the commelina yellow mottle virus (CYMV), (Medberry et al., 1992); the cauliflower mosaic virus (CaMV), (Lawton et al., 1987; Odell et al., 1985); the soya bean chlorotic mottle virus (SoyCMV), (Hasegawa et al., 1989); the figwort mosaic virus (FMV, strain DxS) (Gowda et al., 1989, Malti et al., 1997); FMV strain M3 (Sanger et al., 1990); the cassava vein mosaic virus (CVMV), (Verdaguer et al., 1996), and the peanut chlorotic streak virus (PC1SV), (Maiti and Shepherd, 1998).

Mirabilis mosaic virus (MMV), a member of the genus caulimovirus, has a circular double-stranded DNA genome of about 8 kb pairs with four single-stranded discontinuities in the DNA, one in the α-strand and three in the complementary strand (Richins and Shepherd, 1983). It infects Mirabilis plant species (family Nyctaginaceae) generally found in warm parts of North America. The MMV was characterized as a member of caulimovirus based upon morphology of its virions and inclusion bodies (Brunt and Kitajima, 1973). MMV is serologically distinct from cauliflower mosaic virus, the type member of the genus (Brunt and Kitajima, 1973). The restriction enzyme map of the MMV genome is also quite different than that of other members of this genus (Richins and Shepherd, 1983).

SUMMARY OF THE INVENTION

The present invention is an MMV FLt promoter DNA sequence that can be used to direct and express selected foreign genes in plant cells and plants to confer useful properties therein. The present invention thus provides the isolation and characterization of the full length transcript (FLt) promoter from mirabilis mosaic caulimovirus.

The present invention is also optimal portions of the MMV FLt promoter DNA sequence that permit maximum promoter activity. In accordance with this embodiment, the present invention provides a 360 bp fragment (sequence −297 to +63 from the transcription start site (SEQ ID NO:4)) of the MMV FLt promoter DNA sequence.

The present invention is also the use of the MMV FLt promoter DNA sequence or optimal portions thereof in the form of a single sequence or in the form of multiple enhancer domains to express chimeric genes in plant cells and plants. The present invention is thus a chimeric gene construct containing the MMV FLt DNA sequence or a functional equivalent thereof (i.e., fragments thereof capable of promoter activity) in the form of a single MMV FLt DNA sequence or multiple enhancer domains of the MMV FLt DNA sequence and a coding sequence for a protein of interest; an expression vector containing the chimeric gene construct; a plant cell transformed with the chimeric gene construct; a plant seed transformed with the chimeric gene construct; a plant tissue transformed with the chimeric gene construct; and a transgenic plant transformed with the chimeric gene construct.

The present invention is also the use of the MMV FLt promoter DNA sequence, a functional equivalent thereof, in the form of a single sequence or multiple enhancer domains thereof, in combination with other promoters, e.g., FMV, PC1SV and CaMV 35S, having nonhomologous sequences to introduce two or more proteins of interest into plants and plant cells. The use of promoters having nonhomologous sequences avoids genetic instability due to recombination between identical promoter sequences.

The present invention is also the transcription start site (TSS) of the MMV FLt promoter as determined by primer extension analysis using total RNA isolated from transgenic plants containing a MMV promoter:uidA fusion gene. Analysis of the 5' and 3' deletion constructs show that an upstream region (sequence −248 to −193 from the transcription start site (SEQ ID NO:2)) is very important for the MMV FLt promoter activity along with as-1, TATA box regions. In addition, the present invention is a 31 bp sequence (+33 to +63 from the transcription start site (SEQ ID NO:3)) located downstream of a TATA box that provides for the maximum expression of the MMV FLt promoter.

Additional advantages of the present invention will be set forth in the description and examples that follow, or may be learned from practicing the invention. These and other advantages may be realized and attained by means of the features, instrumentalities and/or combinations particularly described herein. It is also to be understood that the foregoing general description and the following detailed description are only exemplary and explanatory and are not to be viewed as limiting or restricting the invention as claimed.

The invention itself, together with further advantages, will best be understood by reference to the following detailed description, taken in conjunction with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows the DNA sequence of the full length transcript promoter from mirabilis mosaic virus (MMV) in the 5' to 3' direction (SEQ ID NO: 1). The TATA-box (TATATAA), the CAT-box (CAAT), the polyA signal (AATAAA) are shown in bold; all the repeat sequence domains including as-1 and as-2 motifs listed in Table 1 (below) (Designated domains: 1a, 1b; 2a, 2b; 3a, 3b; 4a, 4b; 5a, 5b; 6a, 6b; 7a, 7b; 8a, 8b; 9a, 9b; 10a, 10b (SEQ ID NO:6); 11a, 11b, 11c; 12a, 12b; 13a, 13b; 13a, 13b, 13c; 14a, 14b; 15a, 15b (SEQ ID NO:7); 16; 17; 18; 19a, 19b (SEQ ID NO:8); 20a, 20b & 20c (SEQ ID NO:9)) are underlined or overlined. The end points for the 5' or the 3' deletion plasmids are indicated above or below the sequence respectively. The transcription start site (TSS) is indicated as +1.

(Numbers 1 to 16 (SEQ ID NO:11 THROUGH SEQ ID NO:26)) shows histochemical localization of GUS activity in transgenic tobacco seedlings (magnification X10) representing each construct #1 to 16 (SEQ ID NO:11 THROUGH SEQ ID NO:26), respectively. GUS staining was most intense with construct # 12 (SEQ ID NO:22) followed by construct # 13 (SEQ ID NO:23) and #11 (SEQ ID NO:21). Construct #10 (SEQ ID NO:20), devoid of TATA box, showed no GUS activity and construct #8 (SEQ ID NO:18), devoid of upstream sequence (−133 to −193), showed very little GUS activity. (#17) Untransformed control, wild type N. tabacum cv Samsun NN 24-day-old seedling (magnification X10), no GUS activity was detected.

Figures 4A, 4B:
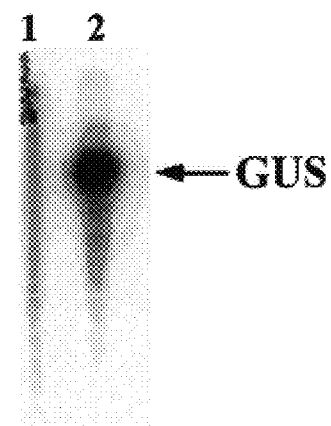

FIG. 4(A) shows RNA-dot hybridization analysis of total RNA (10 μg) isolated from 24-day-old seedlings developed for each construct # 1 to 16 (SEQ ID NO: 11 THROUGH SEQ ID NO: 26). Total RNA was isolated from the best GUS-expressing independent line.

FIG. 4(B) shows Northern analysis of total RNA isolated from untransformed Samsun NN (lane 1) and transgenic tobacco seedlings (R1 progeny) developed with construct #12 (SEQ ID NO:22), (lane 2). Total RNA was hybridized with $^{32}$P-labeled GUS coding sequence.

Figure 5:
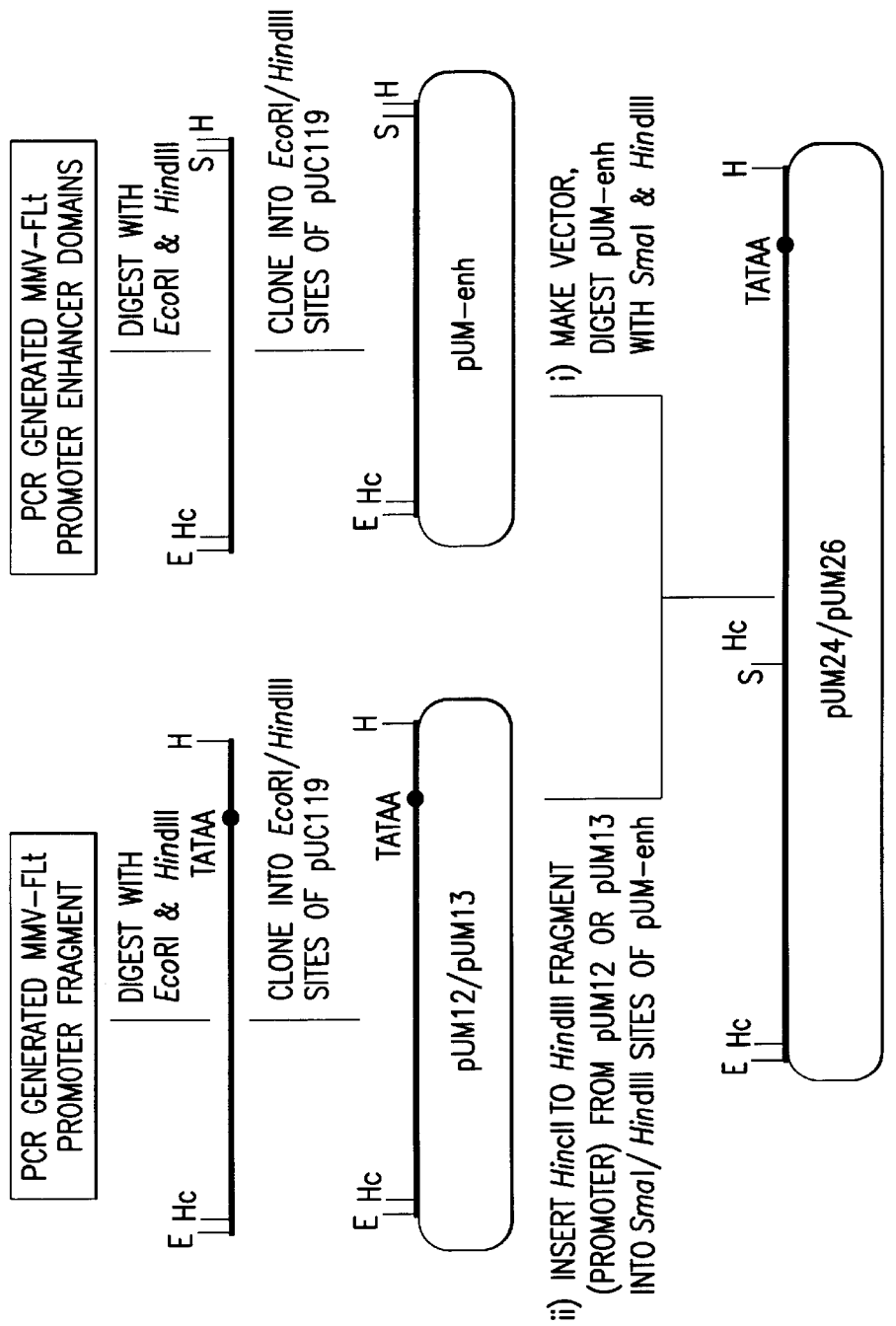

FIG. 5 shows construction strategy for duplicating enhancer domains of the MMV FLt promoter. The EcoRI (E), HindIII (H), SmaI (S) and HincII (Hc) restriction sites used for cloning, and the relative position of TATA sequence are shown. In pUM24 and pUM26, SmaI and HincII sites (SmaI/HincII) are modified.

FIG. 6 shows a schematic representation of GUS constructs used for analyzing expression of the MMVFLt and CaMV 35S promoters in transgenic plants. The respective promoter for each construct is presented. The position of restriction sites used to assemble these expression constructs are shown; GUS represents the gene for the β-glucuronidase of E. coli. The left and right T-DNA border (LB and RB respectively), the rbcS and Nos polyadenylation signal (Terminators) and the Kan$^R$ genes are illustrated.

Figure 7A:
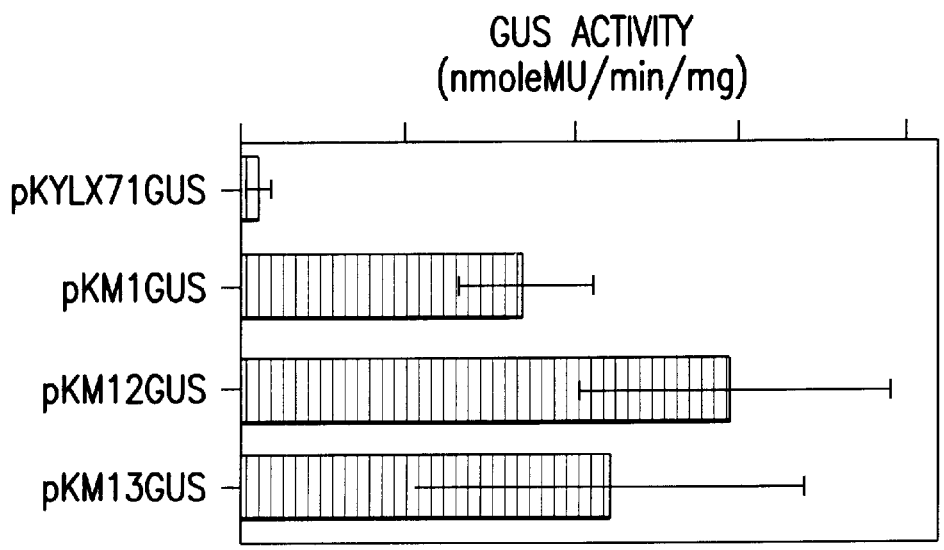
Figure 7B:
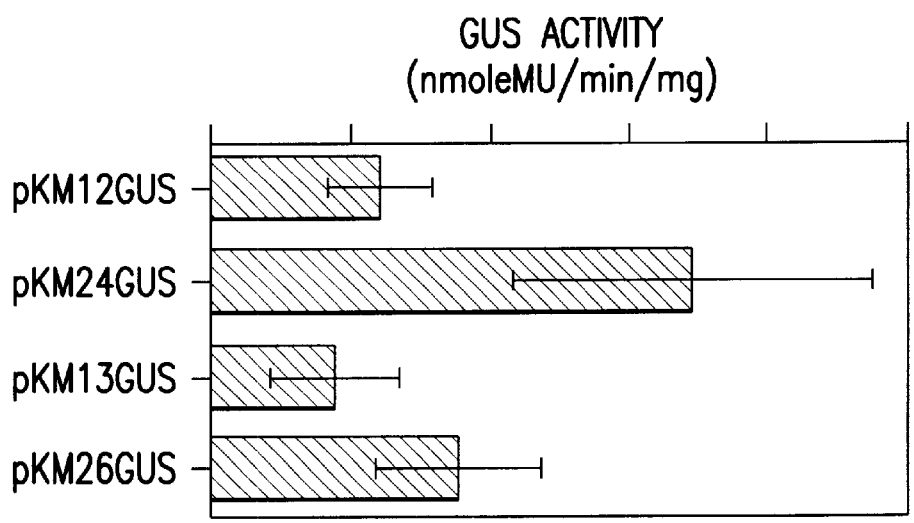

FIGS. 7(A) and 7(B) show comparative expression analysis of the CaMV 35S and the MMV FLt promoters with single and duplicated enhancer domains, in transgenic plants of N. tabacum cv. Samsun NN (R1 progeny). FIG. 7(A) shows a comparison of the CaMV 35S promoter in construct pKYLX71GUS and MMV FLt promoter in constructs pKM1GUS, pKM12GUS and pKM13GUS, directing the GUS reporter gene. GUS activity is determined in tissue extract of 24-days-old seedlings (R1 progeny/second generation). Seedlings are grown in presence of kanamycin (200 mg/ml). The 5' and 3' ends of each MMV FLt promoter in pKM1GUS, pKM12GUS and pKM13GUS are shown in parentheses (−457 to +133 (SEQ ID NO:11)) (−297 to +63 (SEQ ID NO:22)) and (−248 to +63 (SEQ ID NO:23)) respectively. At least twelve independent lines were generated for each construct. The presented value is the mean±SD of three samplings from each of eight independent lines developed for each construct. The MMV FLt promoter activity is significantly different (P<0.0001) from the value observed for the CaMV 35S promoter. FIG. 7(B) shows a comparison of wild type and modified MMV FLt promoter activity in independent transgenic plants of Nicotiana tabacitin cv. Samsun NN (24-days-old seedlings, R1 progeny/ second generation) expressing a GUS reporter gene. At least twelve independent lines were generated for the following GUS-constructs: pKM12GUS and pKM13GUS with the wild type MMV FLt promoter containing a single enhancer domain, and pKM24GUS and pKM26GUS with a modified MMV FLt promoter containing duplicated enhancer domains. The presented value is the mean of three sampling from each of eight independent lines developed for each construct; average GUS activity is presented as the histogram with the standard deviation from the mean indicated by an error bar. The two-tailed P value for pKM12GUS Vs pKM24GUS, and pKM13GUS Vs pKM26GUS is 0.0027 and 0.0079, respectively, is considered very significant.

Figure 8A:
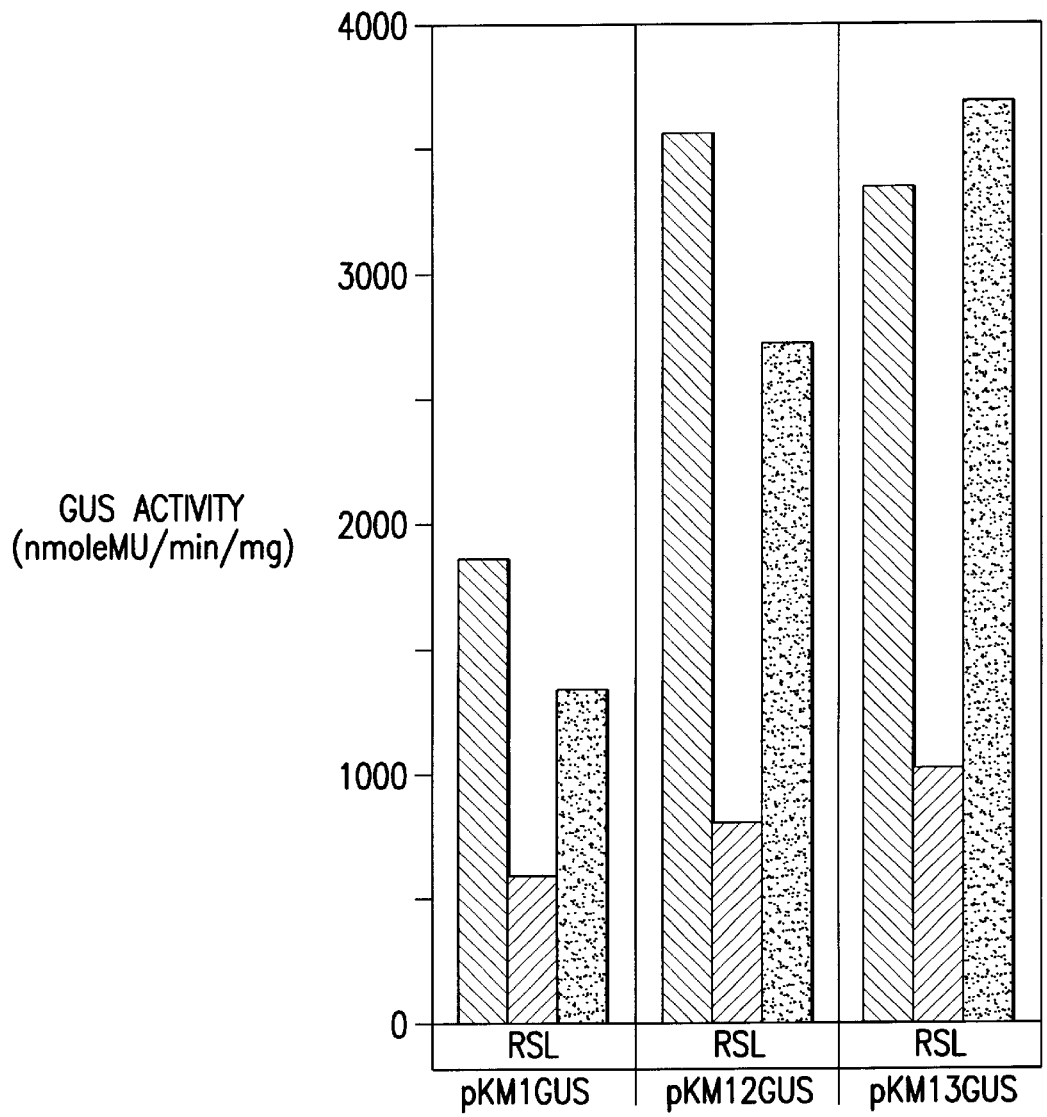
Figure 8B:
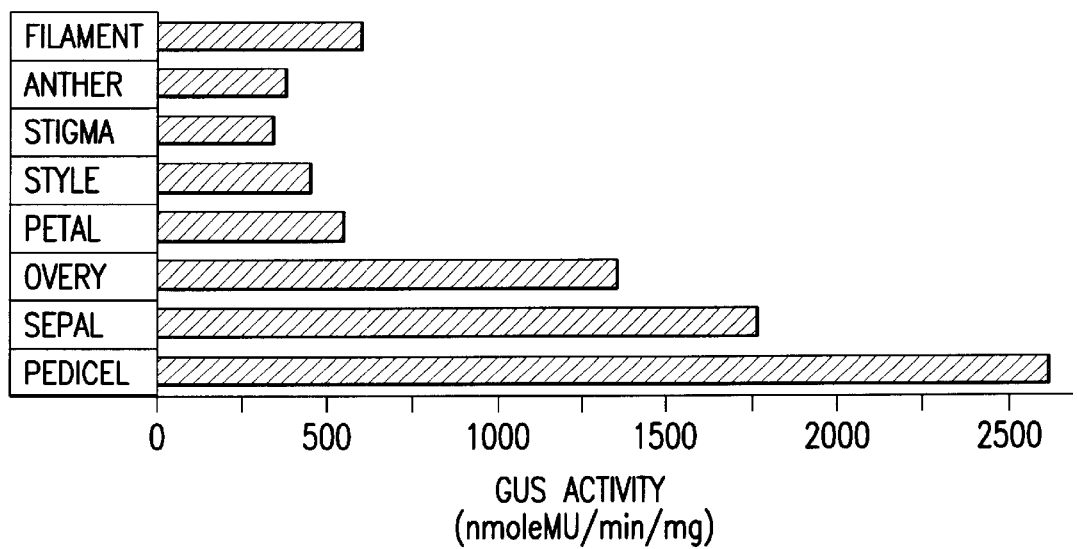

FIGS. 8(A) and 8(B) show expression activity of MMV FLt promoter in various parts of seedlings and different flower organs. FIG. 8(A) shows the MMV FLt promoter activity in different parts of transgenic tobacco seedlings (N. tabacum cv Samsun NN, 24-days-old) as assayed by measuring GUS activity in tissue extracts of roots (R), stems (S) and leaves (L) of seedlings developed for the following constructs: pKM1GUS, pKM12GUS and pKM13GUS. The presented value is the average of seven samplings from each of eight independent lines developed for each construct; variation was within 30% of the presented value. FIG. 8(B) shows MMV FLt promoter activity in different floral organs. GUS activity was measured in each tissue extract as indicated. Tobacco flowers, one day before anthesis, were sampled from transgenic tobacco plants (R0 progeny) developed for the construct pKM12GUS expressing the GUS gene directed by MMV FLt promoter (−297 to +63 (SEQ ID NO:22)). Each sample was assayed four times in three independent experiments. The average GUS activity is presented in the histogram; the variation was within 25% of the presented value.

FIGS. 9(A)–9(K) show histochemical localization of GUS activity in developing transgenic tobacco plants expressing the GUS reporter gene directed by MMV FLt promoter. All sections are at 15× magnification.

FIG. 9(A) shows mature leaf section from six-week-old plants (R1 progeny) developed for construct pKM12GUS; note more GUS staining in vascular tissue (v), midrib and veins.

FIG. 9(B) shows root from four-week-old seedlings (pKM12GUS, R1 progeny), staining is most intense at the tip and in vascular tissue.

FIGS. 9(C), 9(D), and 9(E) show transverse stem section (C), and longitudinal stem section (E), from four-week-old seedlings (pKM12GUS, R1 progeny); GUS activity localized mostly in vascular (v) tissues. No GUS activity with non-transformed control transverse stem (D).

FIG. 9(F) and FIG. 9(G) show transverse section of petiole (F), from four-week-old seedlings (pKM12GUS, R1 progeny), GUS staining is most intense in the vascular (v) system. Transverse section of petiole (G), from four-week-old non-transformed Samsun NN seedlings, no GUS staining was detected.

FIG. 9(H) shows transgenic tobacco seedlings (pKM12GUS, R1 progeny) at 6 DAI grown axenically on agar plate, GUS activity is localized primarily in the root, root tip and lower hypocotyl.

FIG. 9(I) shows transverse section of tobacco ovary: ovule (ov) and placenta (P) are stained most intensely.

FIG. 9(J) shows anther, and 9(K) shows flower tissue; the style and the petal display GUS staining.

DETAILED DESCRIPTION OF THE INVENTION

All patents, patent applications and literatures cited in this description are incorporated herein by reference in their entirety.

As used throughout this application, SEQ ID NO:4 and SEQ ID NO:22 are interchangeably used because they identify identical sequences.

As used throughout this application, SEQ ID NO:4 and SEQ ID NO:22 are interchangeably used because they indentify indentical sequences.

The present invention is the identification and characterization of the full-length transcript (FLt) promoter (SEQ ID NO:1) from the mirabilis mosaic virus (MMV), a newly described member of the caulimovirus group. The short segment of the viral genetic material (MMV FLt promoter sequence) used in this invention does not infect plants or other organisms to cause disease. The DNA sequence is thus useful to direct and express selected foreign genes in plants to confer useful properties to transgenic plants.

The optimal boundaries required for maximum promoter activity are defined by the 5'- and 3'-end deletion analysis of promoter/leader region of the full-length transcript promoter of MMV in transgenic tobacco plants. A 360 bp MMV FLt promoter fragment (sequence –297 to +63 from transcription start site (SEQ ID NO:22)) is sufficient for strong constitutive promoter activity. In a comparative expression analysis, the MMV FLt promoter is found to be approximately 15 to 24 times stronger than the CaMV 35S promoter. The patterns of MMV FLt-directed GUS gene expression are analyzed in transgenic seedlings and matured plants at various stages of development. Plant expression vectors are adapted with the MMV FLt promoter having single and duplicated enhancer domains. The duplication of the upstream enhancer domains increases the promoter activity by at least 2 to 3 fold. In plant metabolic engineering where multiple genes need to be expressed in a single cell, the use of a different promoter with a non-homologous sequence is useful in order to avoid genetic instability due to recombination between identical promoter sequences. Promoters from other member of the caulimovirus group such as MMV, FMV, PC1SV as well as the CaMV 35S promoter are thus very effective in plant genetic engineering applications.

Plant genetic engineering techniques allows researchers to introduce heterologous genes of interest into plants cells to obtain the desired qualities in the plants of choice (Maiti and Hunt, 1992; Wagner, 1992). Plant biotechnology is leading a rapid progress in the production of economically valuable germplasm with improved characteristics or traits such as insect resistance, virus resistance, fungal resistance, herbicide resistance, bacterial or nematode pathogen resistance, cold or drought tolerance, improved nutritional value, seed oil modification, delayed ripening of fruit, and male sterility, to name a few. These germplasms provide enhanced development in breeding programs for crop improvement as well as a better understanding of gene regulation and organization in transgenic plants. The expression of useful foreign traits in plants is a major focus in plant biotechnology.

Plant metabolic engineering is the application of genetic engineering methods to modify the nature of chemical metabolites in plants. For metabolic engineering where multiple genes need to be inserted into one cell, the use of different strong constitutive promoters is desirable in order to avoid genetic instability caused by recombination between identical or closely related promoter sequences, for example, those taken from plants themselves. Through use of these promoter sequences, the introduced genes can be transcribed to messenger RNA and then translated to resultant proteins to exhibit new traits or characteristics.

Besides developing useful traits in crops, plant metabolic engineering provides further understanding of molecular pathways involved in disease development and secondary metabolism in plants. Moreover, by engineering plants with specific foreign genes, the responses of plants to abiotic and biotic stress and stress related metabolism can be analyzed. The present invention, which involves developing gene vectors with newly defined promoters of the caulimoviruses, advances this effort.

A wide variety of well-characterized genes of animal, human, bacterial and plant origin, including those of several viruses, are available for engineering plants. For the most effective expression of this wide selection of genes either constitutive or regulated, versatile gene expression vectors are required. At the University of Kentucky, Dr. Arthur Hunt and his colleagues have developed a series of plant expression vectors (Schardl, et al., 1987) with a constitutive 35S promoter from cauliflower mosaic virus (CaMV), which have been successfully used to produce transgenic plants (Maiti et al., 1988, 1989, 1991, 1991a, 1992, 1992a, 1993, 1994, 1995, 1995a; Graybosh, et al., 1989; Berger, et al., 1989; Yeargan, et al., 1992; Liod, et al., 1992). In accordance with the present invention, useful promoters from MMV for high level expression of foreign genes in transgenic plants are developed. These vectors are useful for both direct DNA uptake by isolated protoplasts and Ti plasmid-mediated gene transfer.

Enhanced levels of transcription via highly active promoters are essential for high levels of gene expression. The most widely used promoter for plant transformation, as described earlier, has been the 35S promoter of CaMV. It is active in a wide variety of plants and tissues. It is also the most thoroughly characterized promoter with respect to the sequence elements active in its transcriptional activity. (Benfey and Chua, 1990). Kay, et al., 1987 showed that the transcriptional activity of the CaMV 35S promoter could be increased approximately 10-fold by making a tandem duplication of 250 base pairs of upstream sequence. Similar observations have been made with other promoters (McNeall, et al., 1989). Earlier, the present inventors constructed and tested a similar construct with the full-length transcript promoters from FMV (Maiti et al., 1997; U.S. patent application Ser. No. 08/675,090, now U.S. Pat. No. 5,994,521), and from PC1SV (Maiti and Shepherd, 1998; U.S. Pat. No. 5,850,019).

The Monsanto Co. has recently patented the 35S and the 19S promoters of CaMV (U.S. Pat. Nos. 5,352,605 and 5,530,196, respectively) and the full length transcript promoter from FMV (U.S. Pat. No. 5,378,619).

A conventional gene of DNA is composed of a promoter region, a 5' non-translated leader sequence of the transcribed messenger RNA, the structural gene itself and a 3' polyadenylation sequence. The promoter is a DNA fragment composed of modular sequence which directs and regulates the transcription to messenger RNA, the first step in expression of a gene. The proper regulatory signals/enhancer elements must be present in a defined location in order to express the inserted gene first into RNA and then into a resultant protein via the process of translation. The 3'-polyadenylation sequence is a non-translated region which signals the adenylation of the 3' end of the RNA in order to stabilize the RNA in the cytoplasm for subsequent translation into protein.

Certain promoters have a specific modular sequence, which makes them either tissue specific, developmentally regulated or environmentally regulated for selective expression of genes in cells. Promoters capable of directing RNA synthesis at higher rates compared to other promoters are desirable for many purposes. Each promoter has a different DNA sequence and is hence unique. Consequently, it will exhibit different activities (strength) under a variety of conditions and circumstances from other promoters. Promoters that are able to direct the expression of genes in most types of tissues in plants are defined as constitutive promoters. Previous work established that the CaMV 35S promoter is one of the strongest constitutive promoters. The transcriptional activity of the CaMV 35S promoter is the result of a synergistic and combinatorial effect of enhancer elements residing upstream of the TATA element. Single or multiple copies of the enhancer sequences from the CaMV 35S promoter can also increase the activity of heterologous promoter in an orientation-independent manner. The enhancement of promoter activity relates to the copy number of the enhancer sequence.

The present invention relates to promoters from mirabilis mosaic virus (MMV) and the use thereof to direct the expression of genes in plant cells and plants.

The present invention includes expression vectors containing the MMV promoter with its single and duplicated enhancer domains. The upstream enhancer elements of the strong constitutive promoter from the full length transcript of MMV is doubled in a strategy to strengthen the promoter even further.

An objective of the present invention is to define and document the strong constitutive FLt promoter of MMV to be used for expression of chimeric genes in transgenic plants. A further object is to describe a strategy to further strengthen the promoter for the full-length transcript of other member of the caulimoviruses including MMV.

The present invention thus includes the following: i) the isolation and mapping of the promoter for the full length transcript (FLt) from mirabilis mosaic virus from a full length viral DNA clone; ii) the modification, including the duplication or multimerization of the enhancer domain of the FLt promoter from the MMV; and iii) the use of the MMV FLt promoter in a method for transforming plant cells with the expression vectors created with wild type and modified MMV FLt promoters directing chimeric genes in transgenic plants, plant tissues, plant cells and plant seeds and their progeny.

Experimental Procedures

Isolation of MMV FLt promoter fragments and construction of plant expression vectors The plasmid pMMV-B10, a full-length genomic clone of MMV (Richins and Shepherd, 1983) has been fully sequenced (Maiti, 1996, unpublished data). A 590 bp segment (coordinates 6621 to 7210 of the MMV genome) was selected for MMV promoter deletion analysis. A series of promoter fragments included in constructing the plant transformation vector with the MMV FLt promoter were designed to study the influence of the upstream and downstream repeat sequences with respect to the TATA-box. The defined MMV FLt promoter sequence, of length as indicated (see in FIG. 2A) was amplified by PCR using appropriately designed oligonucleotides to tailor EcoRI at the 5'-end and HindIII sites at the 3'-end positions. The plasmid pMMV-B10, a genomic DNA clone of MMV (Richins and Shepherd, 1983) was used as template for PCR reaction. PCR amplification was carried out for 30 cycles under the following standard condition; denaturation (92° C. for 1 min), annealing (55° C. for 1 min), synthesis (72° C. for 2 min) using recombinant TaqDNA polymerase (GIBCO BRL). Each of these appropriately sized PCR-generated MMV promoter fragments # 1 to 16 (SEQ ID NO: 1 THROUGH SEQ ID NO: 26) was restricted with EcoRI and HindIII, the restricted fragment was gel purified and cloned into the corresponding sites of pUC119 for DNA sequencing. Before use, all PCR products cloned into pUC119 were sequenced by dideoxy chain terminator method (Sanger et al., 1997) using synthetic primers. Subsequently the promoter fragments were isolated after restriction from pUC119 plasmids. Each of these promoter fragments was gel purified and cloned into the plant expression vector pKYLX 71 (Schardl et al., 1987) at its unique EcoRI and HindIII sites that flank the promoter. The following deletion plasmids were developed; the 5'- and 3' ends of the promoter fragments are given in parenthesis: pKM1 (−457 to +133 (SEQ ID NO:11)), pKM2 (−418 to +133 (SEQ ID NO:12)), pKM3 (−378 to +133 (SEQ ID NO: 13)), pKM4 (−340 to +133 (SEQ ID NO: 14)), pKM5 (−297 to +133 (SEQ ID NO:15)), pKM6 (−248 to +133 (SEQ ID NO:16)), pKM7 (−193 to +133 (SEQ ID NO: 17)), pKM8 (−133 to +133 (SEQ ID NO:18)), pKM9 (−78 to +133 (SEQ ID NO: 19)), pKM10 (−297 to −38 (SEQ ID NO:20)), pKM11 (−457 to +63 (SEQ ID NO:21)), pKM12 (−297 to +63 (SEQ ID NO:22)), pKM13 (−248 to +63 (SEQ ID NO:23)), pKM14 (−193 to +63 (SEQ ID NO:24)), pKM15 (−297 to +2 (SEQ ID NO: 25)) and pKM16 (−287 to +33 (SEQ ID NO: 26)). These plant expression vectors have multiple cloning sites (MCS): 5'-HindIII-BamHI-XhoI-SstI-XbaI-3') with the following unique sites: HindIII, XhoI, SstI and XbaI. The reporter GUS gene was tailored by PCR to include just the coding sequence with the initiation and termination codons, flanked by a XhoI site at the 5' end and a SstI site at the 3' end. The PCR isolated fragment for the GUS reporter gene was digested with XhoI and SstI, gel purified and cloned into the corresponding sites of the pBS(KS+); the resulting plasmid was named pBSGUS. The GUS gene in pBSGUS was fully sequenced before use. The GUS gene from pBSGUS as XhoI-SstI fragment was inserted into the above mentioned pKYLX-based plant expression vectors and the resulting deletion plasmids (constructs # 1 to 16 (SEQ ID NO: 11 THROUGH SEQ ID NO: 26) in FIG. 2A) were designated as pKM1GUS, pKM2GUS, pKM3GUS, pKM4GUS, pKM5GUS, pKM6GUS, pKM7GUS, pKM8GUS, pKM9GUS, pKM10GUS, pKM11GUS, pKM12GUS, pKM13GUS, pKM14GUS, pKM15GUS and pKM16GUS, respectively. The XhoI-GUS-SstI fragment from pBSGUS was inserted into the corresponding sites of pKYLX71 (Schardl et al., 1987). The resulting plasmid pKYLX71 GUS contains the GUS gene directed by the CaMV35S promoter.

Construction of Plasmids for Transient Expression in Protoplasts

The following fragment: 5'-EcoRI-CaMV 35S.2 Promoter-HindIII-BamHI-XhoI-PstI-SstI-XbaI rbcS 3' terminator-ClaI-3' was isolated from pKYLX7135S.2 (Schardl et al., 1987) and cloned into the EcoRI and AccI sites of the pUC119ΔH (a modified pUC119 in which the unique HindIII site was destroyed by digesting with HindIII, and filled with Klenow followed by ligation). The resulting plasmid was named pUCPMA. The GUS reporter gene from pBSGUS as XhoI and SstI fragment was inserted into the corresponding sites of pUCPMA to generate the plasmid pUCPMAGUS. The MMV FLt promoter fragments were cloned into the unique EcoRI and HindIII sites of transient expression vector pUCPMAGUS that flanks the promoter. The resulting PUC-based deletion plasmids (corresponding construct # 1 to 16 (SEQ ID NO:11 THROUGH SEQ ID NO:26 in FIG. 2A) were designated as pPM1GUS, pPM2GUS, pPM3GUS, pPM4GUS, pPM5GUS, pPM6GUS, pPM7GUS, pPM8GU, pPM9GUS, pPM10GUS, pPM11GUS, pPM12GUS, pPM13GUS, pPM14GUS, pPM15GUS, pPM16GUS, respectively.

EXAMPLE 1

Figure 2A:
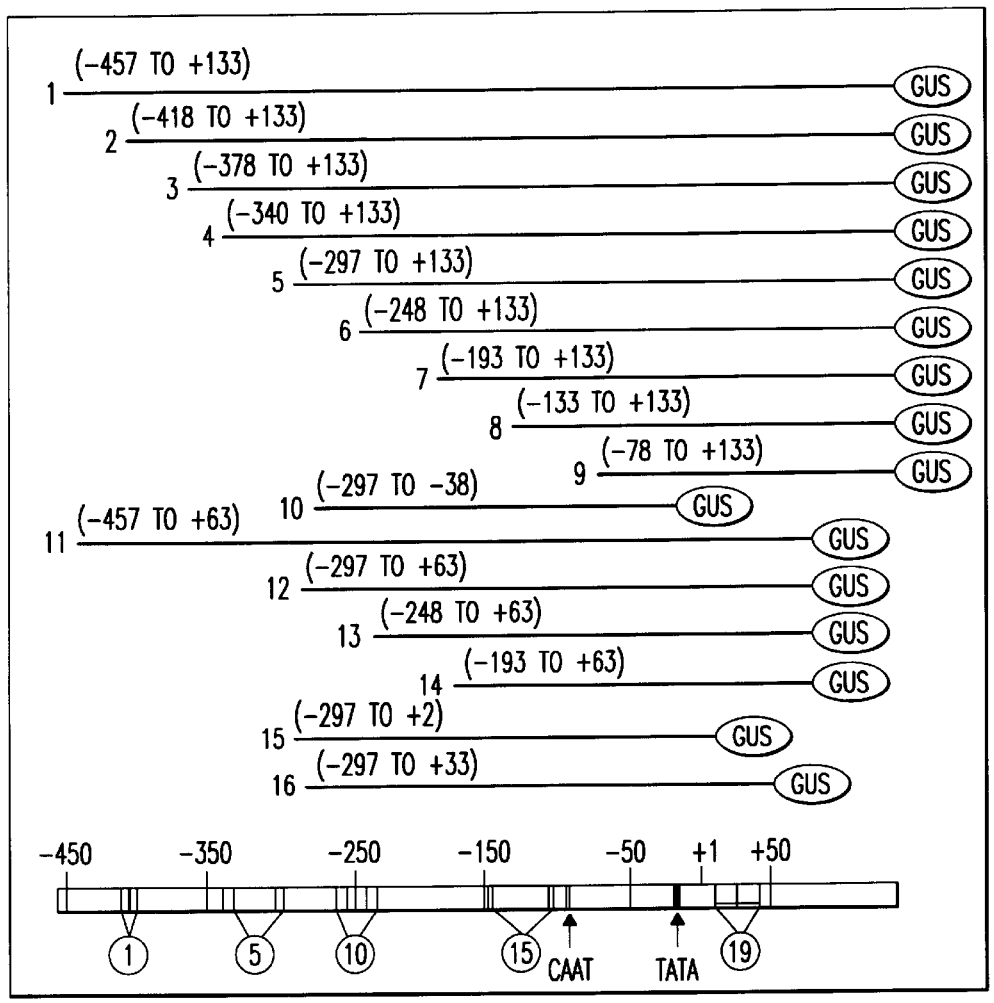
FIG. 2A shows a schematic map of the GUS constructs (number 1 to 16 (SEQ ID NO: 11 THROUGH SEQ. ID. NO.: 26)) developed for 5' and 3' deletion analysis of MMV FLt promoter. The coordinates of the relative deletion fragment are indicated in the parenthesis. At the bottom, the relative positions of the TATA-box, CAAT box, transcription starts site (+1) and direct repeats sequences (listed in Table 1, numbered in circle) are shown.

Expression Analysis of the MMV FLt Promoter Deletion Constructs in Transgenic Plants and in Protoplast Transient Expression Experiments A deletion analysis scheme is shown in FIG. 2A. A series of 5'- and 3'-end-deleted promoter fragments were included in constructing the plant transformation vector with the MMV FLt promoter in order to define the boundaries required for maximal expression from the promoter/leader region and also to study the influence of the upstream and downstream repeat sequences with respect to the TATA-box. The defined MMV promoter fragments # 1 to 16 (SEQ ID NO: 11 THROUGH SEQ ID NO: 26) (as indicated in FIG. 2A) were amplified by PCR and cloned into plant expression vector as described in Experimental Procedures. The resulting plasmids contain the defined promoter sequences # 1 to 16 (SEQ ID NO: 11 THROUGH SEQ ID NO: 26) as described in FIG. 2A. The upstream and downstream deletion end points of the promoter fragment in each plasmid are indicated in parenthesis (FIG. 2A). The various constructs with a reporter gene inserted into the multiple cloning clusters (GUS gene in this case) were tested in transgenic plants (R0 and R1 progeny) and also in protoplast transient expression assay.

At least 10 to 12 independent primary transgenic tobacco (Nicotiana tabacum cv Samsun NN) lines (R0 progeny) were generated with each of these constructs # 1 to 16 (SEQ ID NO: 11 THROUGH SEQ ID NO: 26), and construct pKYLX71 GUS (FIG. 2A). Seeds were collected from self-fertilized independent lines. Segregation analysis of the marker gene ($Kan^R$) was performed. Individual transgenic tobacco lines showing expected segregation ratio ($Kan^R$: $Kan^S$=3:1) for the marker $Kan^R$ gene were further analyzed. Eight to ten independent lines for each construct showed the expected segregation ratio. The expression of the GUS reporter gene in seedlings (R1 progeny/second generation) with these constructs (FIG. 2(A)) was examined by fluorometric assay of tissue extracts (FIG. 2B) and in protoplast transient expression (FIG. 2(C)). Histochemical GUS staining (FIG. 3) examined the tissue distribution of GUS activity in seedlings (R1 progeny/second generation) developed with these constructs.

The MMV FLt promoter deletion analysis in transgenic plants (FIG. 2B) and in protoplast transient expression assay (FIG. 2C) showed overall a very similar profile. However the GUS activity in protoplast assay is about 200 to 800 times less compared to stably transformed transgenic lines (R1 progeny). Analysis of transgenic lines (R1 progeny) and transient expression assay showed more GUS activity with construct #12 (SEQ ID NO:22) which contains the promoter fragment (coordinate −297 to +63 from TSS, FIG. 1). In transgenic plants the 5'-deletion analysis of MMV FLt promoter fragment # 1 to 9 (SEQ ID NO: 11 THROUGH SEQ ID NO: 19) (FIG. 2A) gave 54%, 47%, 36%, 42%, 47%, 37%, 7.5%, 2.2%, and 4%, respectively, of full activity (compare with construct #12 (SEQ ID NO:22) giving the highest activity, FIG. 2B). Similarly in protoplast transient expression experiments the 5' deletion fragments # 1 to 9 (SEQ ID NO: 11 THROUGH SEQ ID NO: 19) showed 23%, 22%, 21%, 20%, 24%, 14.5%, 11%, 13.6%, and 21.8% of full activity, respectively (compare with construct #12 (SEQ ID NO:22) giving the highest activity, FIG. 2C).

The construct #10 (SEQ ID NO:20), which is devoid of the TATA box, showed very little or no GUS activity indicating the importance of a TATA elements in the MMV promoter sequence. A 360 bp MMV FLt promoter/leader fragment, sequence −297 to +63 from TSS (in construct #12 (SEQ ID NO:22)) was found to be sufficient for maximal GUS expression in transgenic tobacco. The MMV FLt promoter with a longer upstream sequence (−457 to +133, construct #1 (SEQ ID NO:11)) is about 54% less active compared with the promoter fragment (−297 to +63, construct #12 (SEQ ID NO:22)).

Figure 2B:
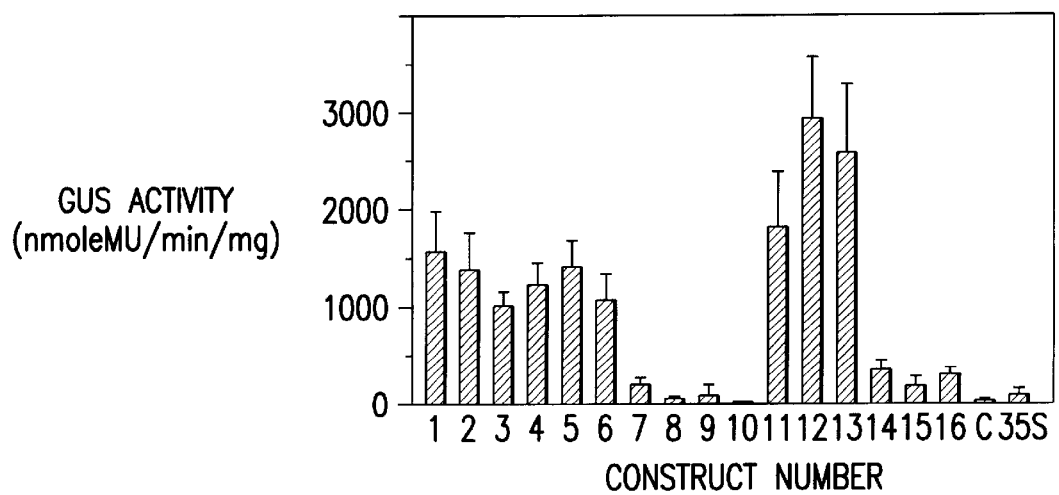
FIG. 2B shows an MMV FLt promoter deletion analysis in transgenic plants expressing the GUS reporter gene. Expression analysis of 5'- and 3'-end deletion constructs (# 1 to 16 (SEQ ID NO: 11 THROUGH SEQ ID NO: 26)) of the MMV FLt promoter in transgenic N. tabacum cv Samsun NN (R1 progeny, 24-day-old seedlings) was conducted. The 5'- and 3'-deletion end points for each construct are as indicated in FIG. 2A. The MMV promoter activity was monitored in 24-day-old seedlings (R1 generation, Kan$^R$) grown aseptically on an MS-agar medium in the presence of kanamycin (200 mg/ml) and 3% sucrose. Soluble protein extracts (5 μg) from whole seedlings were used for GUS assay. The data are means of four independent experiments for each construct (#1 to 16 (SEQ ID NO: 11 THROUGH SEQ ID NO: 26)); eight to ten independent lines for each construct were assayed. The average GUS activity is presented for each chimeric construct in the histogram with the standard deviation from the mean indicated by an error bar. Error bars show the 95% confidence intervals on the means. The statistical (One-way Analysis of Variance, ANOVA) analysis showed the P value<0.0001, considered extremely significant. (C) Untransformed control, tissue extract from wild type N. tabacum cv Samsun NN. (35S) GUS gene directed by the CaMV 35S promoter.
Figure 3:
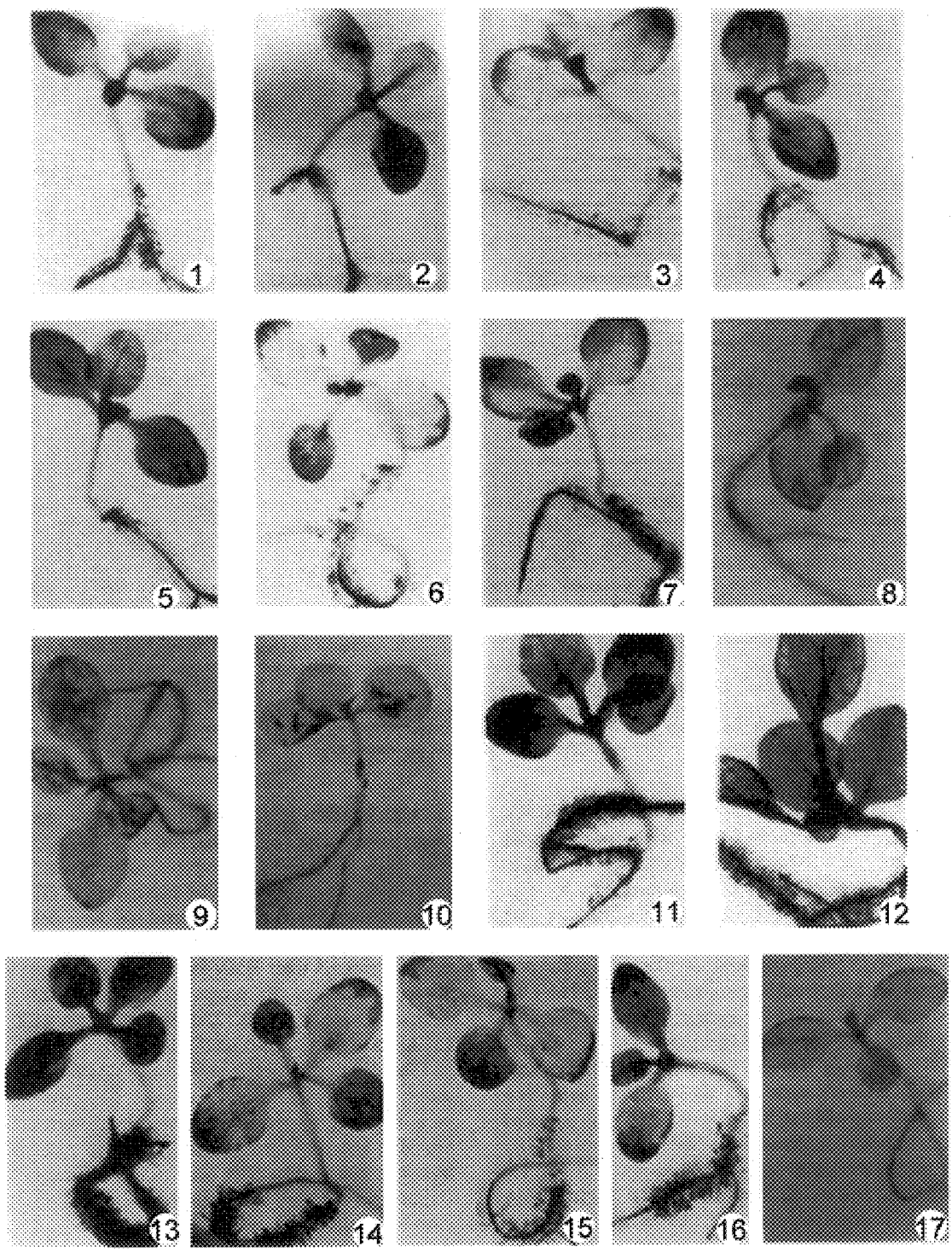
FIG. 3 shows histochemical analysis of GUS expression in tobacco seedlings (transgenic N. tabacum cv Samsun NN, R1 progeny, 24-day-old seedlings) from the best expressing independent line representing each construct # 1 to 16 (SEQ ID NO: 11 THROUGH SEQ ID NO: 26) containing the GUS gene driven by the designated MMV FLt promoter fragment. These data were derived from pools of transformed lines in each construct. The upstream and downstream deletion end points for each construct are as indicated in FIG. 2A.

The strength of the MMV FLt promoter with a GUS reporter gene was evaluated by hybridization analysis of total RNA. Total RNA was prepared from independent transformed tobacco seedlings (R1 progeny) developed for each construct # 1 to 16 (SEQ ID NO: 11 THROUGH SEQ ID NO: 26). Total RNA was hybridized with a $^{32}$P-labeled DNA fragment containing the GUS coding sequence (FIG. 4A). The transcript level was maximum with construct #12 (SEQ ID NO: 22) and was in good agreement with the GUS expression analysis performed by fluorometric assay of total tissue extract (FIG. 2B) and also by histochemical GUS staining of transgenic tobacco seedlings (FIG. 3). The tissue specific expression of GUS in different parts of plants developed for these deletion constructs was not quantitatively evaluated. The Northern analysis of total RNA isolated from transgenic tobacco seedlings (R1 progeny/second generation), developed with construct #12 (SEQ ID NO:22), showed the expected size (2100 nt) of GUS transcript (FIG. 4B).

Figure 2C:
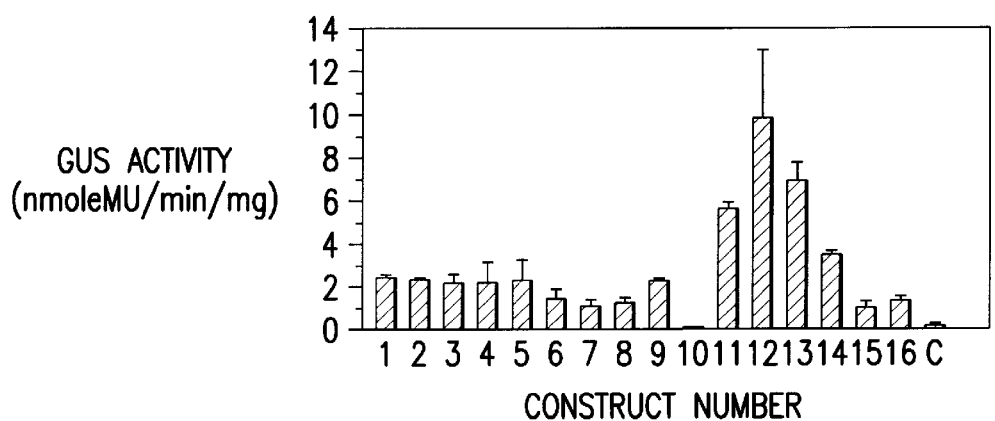
FIG. 2C shows an MMV FLt promoter deletion analysis in protoplast transient expression experiments. The average GUS activity from three independent experiments is presented for each construct in the histogram with the standard deviation from the mean indicated by an error bar. Error bars show the 95% confidence intervals on the means. The statistical ANOVA analysis showed the P value<0.0001, considered extremely significant.

The deletion plasmids containing MMV FLt promoter fragment # 11 and 13 (SEQ ID NO: 21 AND SEQ ID NO: 23) showed 62% and 88% of full activity respectively in transgenic plants (FIG. 2B); and the corresponding value in protoplast transient assay were 57% and 70% of full activity (FIG. 2C; compare with construct # 12 (SEQ ID NO: 22)). In MMV FLt promoter deletion analysis in transgenic plants, the 5' deletion plasmid pKM14GUS (construct #14 (SEQ ID NO:24), promoter coordinate −193 to +63) containing 'as-1' domains and TATA-box sequence, and the 3' deletion plasmid pKM16GUS (construct # 16 (SEQ ID NO:26), promoter coordinate −297 to +33) showed about 13% and 11% of full activity, respectively (compare with plasmid pKM12GUS, construct #12 (SEQ ID NO:22), giving the highest activity, FIG. 2B). The 5' deletion plasmid pKM14GUS (construct #14 (SEQ ID NO:24)) containing 'as-1' domains and TATA-box sequence showed less activity suggesting dependency on additional upstream sequence elements. These results of MMV FLt promoter deletion analysis suggest that a TATA-upstream sequence (coordinate −297 to −193 (SEQ ID NO:10), in FIG. 1) and a TATA-down-stream sequence (coordinate +2 to +63 (SEQ ID NO:27), in FIG. 1) may be involved in regulating function of the full-length transcript promoter. Several direct repeat sequences (# 8a & 8b; #9a & 9b; #10a & 10b (SEQ ID NO:6); # 11a & 11b; as denoted in FIG. 1) are present in the TATA upstream sequence (coordinate −297 to −193 (SEQ ID NO:10), in FIG. 1; and listed in Table 1).

A 19 bp motif having strong homology with the activation sequence 1 (as-1) of the CaMV 35S promoter (Lam et al., 1989) was identified in the MMV promoter at coordinate −64 to −46 (SEQ ID NO:5) relative to TSS. This motif is also found in FMV (Sanger et al., 1990) and CVMV Verdagur et al., 1996). This as-1 motif is able to confer root-specific expression in the CaMV35S promoter (Lam et al., 1989). However the MMV FLt deletion construct #8 and #9 (SEQ ID NO:18 AND SEQ ID NO:19) containing putative as-1 domain showed no appreciable GUS staining in root tips of seedlings, however, GUS expression is clearly evident in leaf regenerating meristem tissue (FIG. 3). More studies will be needed to fully evaluate the function of as-1 domain in the MMV FLt promoter. This as-1 domain plays a more complex role in the regulation of the promoter activity by acting synergistically with other cis-elements (Fang et al., 1989; Lam et al., 1989). It is also reported as a salicylic acid-responsive element (Qin et al., 1994).

The promoter fragment −193 to +133 in construct #7 (SEQ ID NO:17) confers much less promoter activity compared to construct #6 (SEQ ID NO:16) with promoter coordinates −248 to +133 and construct #5 (SEQ ID NO:15) with promoter coordinates −297 to +133 (SEQ ID NO:15) (FIG. 2B). This implies that the upstream sequence −297 to −193 (SEQ ID NO:10) is essential for promoter activity and two repeat sequences in this region (TTGAAGATAAGA, # 10a and 10b in FIG. 1 (SEQ ID NO:6); and listed in Table 1) at positions −265 to −254 and −245 to −234 may be important for promoter activity. More studies including internal deletion mapping will be required to fully analyze the importance of these sequences.

The MMV FLt promoter gives better activity with a longer 3' untranslated region downstream of the promoter's TATA box, extending to +63 compared with +2 and +33, (compare construct #15 and #16 (SEQ ID NO: 25 AND SEQ ID NO: 26) respectively with construct #12, FIG. 2B, FIG. 3 and FIG. 4A). Increaeses in GUS transcript level and also in GUS activity suggest that the 3' untranslated region downstream of MMV FLt promoter's TATA box has some sequence importance for initiation of transcription and concurrent translation. The MMV 3' untranslated region of the promoter may enhance transcription. It has been shown that the 3' untranslated viral regions from CaMV, and tobacco mosaic virus (TMV), (Day Dowson et al., 1993) stimulate the expression of a down stream reporter gene by enhancing translation. The 3' untranslated region of FMV (Maiti et al., 1997) also stimulates the expression of a downstream gene; it needs to be evaluated whether it is due to enhanced transcription or translation.

Two 18-nucleotide direct repeat sequences (#19a and 19b (SEQ ID NO:8) in FIG. 1; and listed in Table 1) and three 10-nucleotide repeat sequences (#20a, 20b and 20c (SEQ ID NO:9) in FIG. 1) are located in the TATA-down-stream sequence, coordinates +2 to +63, (in FIG. 1; Table 1) (SEQ ID NO:5) of the MMV FLt promotor. These repeat sequence domains may have some regulatory functions. As the construct pKM15GUS (construct #15 (SEQ ID NO:25), promoter coordinate −297 to +2) showed much less activity than the pKM12GUS (construct #12 (SEQ ID NO:22), promoter coordinate −297 to +63), this indicates that the repeat sequences AATCGAAATCAAAA (SEQ ID NO:8) at positions +10 to +23 and +28 to +44 are also playing important roles in promoter activity.

The comparative analysis of CaMV 35S-promoter and MMV FLt promoter in transgenic plants (R1 progeny) developed for construct pKYLX71GUS and pKM12GUS, respectively, showed that the MMV FLt promoter is about 25 times stronger than the CaMV 35S promoter (FIG. 2B).

A full-length transcript promoter from the viral genome of mirabilis mosaic virus (MMV), a newly described member of caulimovirus group (Richins and Shepherd, 1983) is thus characterized. The MMV promoter is a strong constitutive promoter able to direct foreign gene expression in transgenic plants. There is limited sequence homology between the MMV FLt promoter and those of CaMV and other caulimovirus promoters although they are functionally analogous, which may imply differences in the mechanisms of promoter regulation. Analysis of the MMV promoter sequence shows the presence of several motifs that resemble previously identified cis elements that are implicated in transcriptional regulation. The presence of such motifs in the MMV promoter sequence could explain the pattern and relative strength of different promoter deletion fragments in transgenic plants.

In accordance with the invention the regulatory region of the MMV FLt promoter and interacting nuclear factors involved in tissue-specific and constitutive expression of genes in plants has been studied. The CaMV 35S promoter is composed of several discrete organ specific cis-elements in the upstream region of the promoter (Lam, 1994). The molecular analysis of the functional interactions between specific cis-elements and cognate trans factor will be essential in developing more active 'super promoter' and modified tissue-specific promoter.

Preparation of Plant Expression Vectors
Construction of a MMV FLt Promoter with a Double Enhancer Element Procedures for isolating MMV FLt promoter fragments and construction of the plant expression vectors (pKM1GUS, pKM12GUS and pKM13GUS) with a MMV FLt promoter containing a single enhancer domain are described above. The MMV FLt promoter fragments were amplified from a full-length clone of MMV as described above. The construction strategy for isolating the MMV FLt promoter and duplicating its enhancer domains is shown in FIG. 5. The following two MMV FLt promoter fragments of 360 bp (−297 to +63 from the transcription start site (SEQ ID NO: 22)) and 311 bp (−248 to +63 (SEQ ID NO:23)) were isolated after amplification by PCR using oligonucleotides containing the appropriate sequence to generate EcoRI and HincII sites at the 5' end and a HindIII site at the 3' end of the fragment. These two promoter fragments were cloned into PUC119 as EcoRI-HindIII fragments. The resulting plasmids were designated as pUM12 and pUM13, respectively. The TATA upstream sequence containing enhancer domains, a 261 bp (position −297 to −38 from the transcription start site (SEQ ID NO:20)) was amplified by PCR with oligonucleotides designed to engineer EcoRI-HincII sites at the 5' end and SmaI-HindIII sites at the 3' end of the fragment. This enhancer fragment was cloned into the EcoRI and HindIII sites of pUC119 and the plasmid was named as pUM-enh. Two MMV FLt promoter fragments of 360 bp and 311 bp were isolated as HincII-HindIII fragments from pUM12 and pUM13, respectively; these fragments were inserted into the SmaI and HindIII sites of pUM-enh. The resulting plasmids designated as pUM24 and pUM26 contain two copies of the enhancer elements. The respective MMV FLt promoter with its duplicated enhancer domain was inserted into the plant expression vector pKYLX71 (Schardl et al., 1987) at its unique EcoRI and HindIII sites that flank the promoter. The resulting expression vectors were designated as pKM24 and pKM26, respectively.

EXAMPLE 2

Comparative Expression Analysis of the CaMV 35S Promoter with the MMV FLt Promoters Containing Single and Duplicated Enhancer Domains In order to compare the relative expression activities of the MMV FLt promoter and the CaMV 35S promoter, we tested the following gene constructs coupled to the GUS reporter gene in stably transformed tobacco plants: pKM1GUS, pKM12GUS and pKM13GUS for the MMV FLt promoter with a single enhancer domain and pKYLX71GUS containing the CaMV35S promoter. A schematic map for each construct is shown in FIG. 6. At least 12 independent primary tobacco lines were generated for each construct. Transformation is carried out using *Nicotiana tabacum* cv. Samsun NN as described earlier (Maiti et al., 1997). The integration of the reporter GUS gene in the genome of transgenic plants (R0 and R1 progeny) was confirmed by PCR analysis (data not shown). A comparative analysis was carried out by assaying the GUS activity in tissue extract of tobacco seedlings (R1 progeny, 24-days-old) expressing the GUS reporter gene. Results are shown in FIG. 7A. The pKM1GUS with the full-length MMV promoter (promoter coordinates −457 to +133 (SEQ ID NO:11)) gave about 15 fold more expression activity compared to the CaMV 35S promoter. Maximally expressing MMV promoter fragment in pKM12GUS with promoter sequence −297 to +63 (SEQ ID NO:22), shows about 24-fold higher promoter expression activity compared to the CaMV 35S promoter. These results suggest that the MMV FLt promoter is relatively more stronger than the CaMV 35S promoter.

EXAMPLE 3
Expression Analysis of the MMV FLt Promoter with Single and Duplicated Enhancer Domains In order to compare the MMV wild type and modified FLt promoters, at least twelve independent transgenic tobacco lines were generated for each construct, pKM24GUS and pKM26GUS (FIG. 7B). Seedlings (R1 progeny, 24-days-old) generated from independent lines giving a 3:1 segregation ratio for the Kan$^R$ marker gene were used for GUS expression analysis. The MMV FLt promoter with duplicated enhancer domains in constructs pKM24GUS and pKM26GUS showed 3- and 2-fold more GUS activity respectively compared to constructs pKM12GUS and pKM13GUS containing single enhancer domain (FIG. 7B). Hence, the MMV FLt promoter with duplicated enhancer domains is more active than the wild-type promoter with a single enhancer domain. The duplication of enhancer domains sequence was also shown to increase the promoter activity by several folds in other caulimovirus promoters (Kay et al., 1987; Maiti et al., 1997; Maiti and Shepherd, 1998).

EXAMPLE 4
Expression of the MMV FLt Promoter in Different Parts of Transgenic Seedlings (R1 Progeny)

The MMV FLt promoter activity was examined in various tissues during seedling development (FIG. 8A). Seedlings were grown aseptically on an MS-agar medium in presence kanamycin of (200 μg/ml) and 3% sucrose. Independent lines showing 3:1 segregation ratio for the Kan$^R$ marker gene were taken for further analysis. Eight independent lines for each construct were studied. The relative expression of the GUS reporter gene in 24-day-old seedlings (R1 progeny/ second generation) transformed with pKM12GUS or pKM13GUS was monitored by fluorometric assay of tissue extract and by histochemical staining of transverse section of leaves, stems and roots. Relative levels of GUS activity in roots, leaves and stems is shown in FIG. 8A. GUS activity for construct pKM12GUS was highest in roots, about 1.5 times more in roots compared to leaves. GUS activity was very comparable in root and leaves for construct pKM13GUS. The lowest level of expression was in stems for both construct tested.

EXAMPLE 5
Expression of the MMV FLt Promoter in Different Floral Organs

MMV FLt promoter activity was examined in different floral organs from several primary independent lines (R0 progeny) developed with pKM12GUS. Flower samples were collected one day before anthesis. Total soluble proteins were extracted from different parts of the flower and subsequently GUS activity was measured flurometrically as described earlier (Maiti et al., 1997). The highest expression was observed in the pedicel followed by ovary, filament, petal (corolla), style, stigma and anthers (FIG. 8B). The activity in flowers is relatively low compared to leaves, stems and roots of the plants. Similar observation was made with the CaMV 35S promoter (An et al., 1988) and FMV FLt promoter (Maiti et al., 1997) in transgenic tobacco plants.

EXAMPLE 6
Histochemical Staining to Determine GUS Accumulation

A detailed histochemical analysis of GUS accumulation shown in FIG. 9, was carried out using hand-cut fresh tissue sections of various organs from transformed plants (R1 progeny) developed for the construct pKM12GUS (FIG. 6). The vascular tissues of young leaves, petioles, roots and stems showed greatest intensity of GUS staining. The histochemical GUS assay of leaves showed more intense staining in midribs, veins and other vascular tissue than in leaf mesophyll and palisade cells. Strong GUS accumulation was detected in phloem tissues in the midrib and lateral secondary veins of matured leaves (FIG. 9A). Cross sections of stems showed intense staining of the phloem cells (FIGS. 9C & 9E). The non-transformed tobacco showed no GUS activity in cross sections of vascular tissue of roots (data not shown), stems or petioles (FIGS. 9D and 9G). Intensity of GUS staining was strongest in root tissues followed by leaves and stems (FIG. 9B). Histochemical GUS assay was also performed with different floral tissues. The petal (corolla) portion of the flower exhibited light staining (FIG. 9K). Anther-containing pollen grains exhibited intense blue staining (FIG. 9J). The stigma and style portion of the flower showed variation in GUS activity staining (data not shown). Pollen grains from mature anthers exhibited blue GUS staining (data not shown). The longitudinal cross-section of the ovary (12 days after opening of the flower), showed intense blue staining of the placenta (the basal vascular part of the ovary) and immature seeds inside the ovary (FIG. 9I). Differential staining intensity in different floral organs suggests the tissue specificity of the MMV FLt promoter.

A full-length transcript promoter from the viral genome of mirabilis mosaic virus, a member of the caulimovirus group (Richins and Shepherd, 1983) is thus characterized. The MMV promoter is a strong, constitutive promoter able to direct foreign gene expression in transgenic tobacco plants at a level higher than that of the CaMV 35S promoter. The MMV FLt promoter is highly expressed in vascular tissues of the stem, in leaf mesophyll cells and in root tips of tobacco plants.

Plant expression vectors are adapted with the MMV FLt promoter with its single and duplicated enhancer domains. In plant metabolic engineering, where multiple genes need to be expressed in a single cell, the use of different promoters with non-homologous sequences will be useful in order to avoid genetic instability due to recombination between identical promoter sequences. Promoters from different caulimovirus group such as MMV, FMV, PC1SV as well as the CaMV 35S promoter are very effective in plant genetic engineering applications.

TABLE 1

A list of DNA repeat sequence domains and tentative regulatory elements (TATA-box, CAAT-box, AATAAA-polyA signal) in the MMVFLt promoter. A notation (nt) denotes number of nucteotides.

| Designated domain | Repeat sequence & regulatory elements | Position (relative to TSS) | Spacing (nt) between successive domains |
|---|---|---|---|
| 1a & 1b. | GGATT | −415 to −411, −407 to −403 | 3 |
| 2a & 2b. | CAACA | −434 to −430, −399 to −395 | 30 |
| 3a & 3b. | TAAT | −427 to −424, −411 to −408 | 12 |
| 4a & 4b. | CAAAAA | −361 −356, −355 to −350 | 0 |
| 5a & 5b. | ACACCA | −339 to −334, −305 to −300 | 28 |
| 6a & 6b. | CACCAGC | −338 to −332, −321 to −315 | 10 |
| 7a & 7b. | GTGTT (invert repeat) | −329 to −325, −312 to −308 | 12 |
| 8a & 8b | TCGTCC | −296 to −291, −272 to −267 | 18 |
| 9a & 9b | ACATC | −286 to −282, −280 to −276 | 1 |
| 10a & 10b | TTGAAGATAAGA* | −265 to −254, −245 to −234 | 8 |
| 11a, 11b & 11c | AGATAA (three repeats) | −261 to −256, −256 to −251, −241 to −236 | 1st & 2nd overlap by 1 nt, 9 nt in 2nd to 3rd |
| 12a & 12b | GATG (as-2 like motif) | −189 to −186, −186 to −183 | overlap by 1 nt |
| 13a, 13b & 13c | GTGAAGC (three repeats) | −166 to −160, −157 to −151, −127 to −121 | 2 nt in 1st & 2nd, 23 nt in 2nd & 3rd |
| 14a & 14b | GTGAAGCAT | −166 to −158, −127 to −119 | 30 |
| 15a & 15b | GGTCCCTCCACT** | −147 to −138, −110 to −99 | 27 |
| 16 | CAAT-box | −91 to −88 | |
| 17. | ATGACGT (as-1 motif) | −64 to −58, −52 to −46 | 5 |
| 18 | TATATAA-box | −24 to −18 | |
| 19a & 19b | AATCGAAATCAAAATCGG*** | +10 to +27, +28 to +45 | 0 |
| 20a, & 20b & 20c | AATCGAAATC (three repeats)**** | +10 to +19, +28 to +37, +46 to +55 | 8 nt, in 1st & 2nd; 8 nt in 2nd & 3rd |

*SEQ ID NO: 6
**SEQ ID NO: 7
***SEQ ID NO: 8
****SEQ ID NO: 9

---

SEQUENCE LISTING

<160> NUMBER OF SEQ ID NOS: 26

<210> SEQ ID NO 1
<211> LENGTH: 721
<212> TYPE: DNA (promoter)
<213> ORGANISM: mirabilis mosaic caulimovirus

<400> SEQUENCE: 1

```
tggagattca gaaaaatctc catcaacaaa taatccaagt aaggattaat ggattgatca      60
acatccttac cgctatgggt aagattgatg aaaagtcaaa aacaaaaatc aattatgcac     120
accagcatgt gttgatcacc agctattgtg ggacaccaat ttcgtccaca gacatcaaca     180
tcttatcgtc ctttgaagat aagataataa tgttgaagat aagagtggga gccaccacta     240
aaacattgct ttgtcaaaag ctaaaaaaga tgatgcccga cagccacttg tgtgaagcat     300
gtgaagccgg tccctccact aagaaaatta gtgaagcatc ttccagtggt ccctccactc     360
acagctcaat cagtgagcaa caggacgaag gaaatgacgt aagccatgac gtctaatccc     420
acaagaattt cctatataa ggaacacaaa tcagaaggaa gagatcaatc gaaatcaaaa     480
tcggaatcga aatcaaaatc ggaatcgaaa tctctcatct ctctctacct tctctctaaa     540
aaacacttag atgtgtgagt aatcacccac ttggggttgt aatatgtagt agtaaataag     600
ggaaccttag ggtataccat tgttgtaata ttattttcag tatcaataaa ataatctttc     660
agtttatctt atattcattt gtgtgacacc gtattcccat aaaaccgatc ctaatctctc     720
c                                                                    721
```

<210> SEQ ID NO 2
<211> LENGTH: 56
<212> TYPE: DNA (promoter)
<213> ORGANISM: mirabilis mosaic caulimovirus

<400> SEQUENCE: 2
atgttgaaga taagagtggg agccaccact aaaacattgc tttgtcaaaa gctaaa        56

<210> SEQ ID NO 3
<211> LENGTH: 31
<212> TYPE: DNA (promoter)
<213> ORGANISM: mirabilis mosaic caulimovirus

<400> SEQUENCE: 3
aaatcaaaat cggaatcgaa atctctcatc t        31

<210> SEQ ID NO 4
<211> LENGTH: 360
<212> TYPE: DNA (promoter)
<213> ORGANISM: mirabilis mosaic caulimovirus

<400> SEQUENCE: 4
ttcgtccaca gacatcaaca tcttatcgtc ctttgaagat aagataataa tgttgaagat        60
aagagtggga gccaccacta aaacattgct ttgtcaaaag ctaaaaaaga tgatgcccga       120
cagccacttg tgtgaagcat gtgaagccgg tccctccact aagaaaatta gtgaagcatc       180
ttccagtggt ccctccactc acagctcaat cagtgagcaa caggacgaag gaaatcacgt       240
aagccatgac gtctaatccc acaagaattt ccttatataa ggaacacaaa tcagaaggaa       300
gagatcaatc gaaatcaaaa tcggaatcga atcaaaatc ggaatcgaaa tctctcatct       360

<210> SEQ ID NO 5
<211> LENGTH: 63
<212> TYPE: DNA (promoter)
<213> ORGANISM: mirabilis mosaic caulimovirus

<400> SEQUENCE: 5
gaagagatca atcgaaatca aaatcggaat cgaaatcaaa atcggaatcg aaatctctca        60
tct        63

<210> SEQ ID NO 6
<211> LENGTH: 12
<212> TYPE: DNA (promoter)
<213> ORGANISM: mirabilis mosaic caulimovirus

<400> SEQUENCE: 6
ttgaagataa ga        12

<210> SEQ ID NO 7
<211> LENGTH: 12
<212> TYPE: DNA (promoter)
<213> ORGANISM: mirabilis mosaic caulimovirus

<400> SEQUENCE: 7
ggtccctcca ct        12

<210> SEQ ID NO 8
<211> LENGTH: 18
<212> TYPE: DNA (promoter)
<213> ORGANISM: mirabilis mosaic caulimovirus

<400> SEQUENCE: 8

-continued aatcgaaatc aaaatcgg					18

<210> SEQ ID NO 9
<211> LENGTH: 10
<212> TYPE: DNA (promoter)
<213> ORGANISM: mirabilis mosaic caulimovirus

<400> SEQUENCE: 9 aatcgaaatc					10

<210> SEQ ID NO 10
<211> LENGTH: 105
<212> TYPE: DNA (promoter)
<213> ORGANISM: mirabilis mosaic caulimovirus

<400> SEQUENCE: 10
ttcgtccaca gacatcaaca tcttatcgtc ctttgaagat aagataataa tgttgaagat     60
aagagtggga gccaccacta aaacattgct ttgtcaaaag ctaaa                    105

<210> SEQ ID NO 11
<211> LENGTH: 590
<212> TYPE: DNA (promoter)
<213> ORGANISM: mirabilis mosaic caulimovirus

<400> SEQUENCE: 11
tggagattca gaaaatctc catcaacaaa taatccaagt aaggattaat ggattgatca      60
acatccttac cgctatgggt aagattgatg aaaagtcaaa acaaaaatc aattatgcac     120 accagcatgt gttgatcacc agctattgtg ggacaccaat ttcgtccaca gacatcaaca    180
tcttatcgtc ctttgaagat aagataataa tgttgaagat aagagtggga gccaccacta    240
aaacattgct ttgtcaaaag ctaaaaaaga tgatgcccga cagccacttg tgtgaagcat    300
gtgaagccgg tccctccact aagaaaatta gtgaagcatc ttccagtggt ccctccactc    360
acagctcaat cagtgagcaa caggacgaag gaaatgacgt aagccatgac gtctaatccc    420
acaagaattt ccttatataa ggaacacaaa tcagaaggaa gagatcaatc gaaatcaaaa    480
tcggaatcga atcaaaatc ggaatcgaaa tctctcatct ctctctacct tctctctaaa    540
aaacacttag atgtgtgagt aatcacccac ttggggttgt aatatgtagt                590

<210> SEQ ID NO 12
<211> LENGTH: 551
<212> TYPE: DNA (promoter)
<213> ORGANISM: mirabilis mosaic caulimovirus

<400> SEQUENCE: 12
taaggattaa tggattgatc aacatcctta ccgctatggg taagattgat gaaaagtcaa     60
aaacaaaaat caattatgca caccagcatg tgttgatcac cagctattgt gggacaccaa    120
tttcgtccac agacatcaac atcttatcgt cctttgaaga taagataata atgttgaaga    180
taagagtggg agccaccact aaaacattgc tttgtcaaaa gctaaaaaag atgatgcccg    240
acagccactt gtgtgaagca tgtgaagccg gtccctccac taagaaaatt agtgaagcat    300
cttccagtgg tccctccact cacagctcaa tcagtgagca acaggacgaa ggaaatgacg    360
taagccatga cgtctaatcc cacaagaatt tccttatata aggaacacaa atcagaagga    420
agagatcaat cgaaatcaaa atcggaatcg aaatcaaaat cggaatcgaa atctctcatc    480
tctctctacc ttctctctaa aaaacactta gatgtgtgag taatcaccca cttggggttg    540

```
taatatgtag t                                                        551

<210> SEQ ID NO 13
<211> LENGTH: 511
<212> TYPE: DNA (promoter)
<213> ORGANISM: mirabilis mosaic caulimovirus

<400> SEQUENCE: 13
taagattgat gaaaagtcaa aacaaaaat caattatgca caccagcatg tgttgatcac     60
cagctattgt gggacaccaa tttcgtccac agacatcaac atcttatcgt cctttgaaga   120
taagataata atgttgaaga taagagtggg agccaccact aaaacattgc tttgtcaaaa   180
gctaaaaaag atgatgcccg acagccactt gtgtgaagca tgtgaagccg gtccctccac   240
taagaaaatt agtgaagcat cttccagtgg tccctccact cacagctcaa tcagtgagca   300
acaggacgaa ggaaatgacg taagccatga cgtctaatcc cacaagaatt ccttatata    360 aggaacacaa atcagaagga agagatcaat cgaaatcaaa atcggaatcg aaatcaaaat   420
cggaatcgaa atctctcatc tctctctacc ttctctctaa aaaacactta gatgtgtgag   480
taatcaccca cttggggttg taatatgtag t                                  511

<210> SEQ ID NO 14
<211> LENGTH: 473
<212> TYPE: DNA (promoter)
<213> ORGANISM: mirabilis mosaic caulimovirus

<400> SEQUENCE: 14
cacaccagca tgtgttgatc accagctatt gtgggacacc aatttcgtcc acagacatca    60
acatcttatc gtcctttgaa gataagataa taatgttgaa gataagagtg ggagccacca   120
ctaaaacatt gctttgtcaa agctaaaaaa gatgatgcc cgacagccac ttgtgtgaag    180
catgtgaagc cggtccctcc actaagaaaa ttagtgaagc atcttccagt ggtccctcca   240
ctcacagctc aatcagtgag caacaggacg aaggaaatga cgtaagccat gacgtctaat   300
cccacaagaa tttccttata taggaacaca aatcagaag gaagagatca atcgaaatca   360
aaatcggaat cgaaatcaaa atcggaatcg aaatctctca tctctctcta ccttctctct   420
aaaaaacact tagatgtgtg agtaatcacc cacttggggt tgtaatatgt agt          473

<210> SEQ ID NO 15
<211> LENGTH: 430
<212> TYPE: DNA (promoter)
<213> ORGANISM: mirabilis mosaic caulimovirus

<400> SEQUENCE: 15
ttcgtccaca gacatcaaca tcttatcgtc ctttgaagat aagataataa tgttgaagat    60
aagagtggga gccaccacta aaacattgct ttgtcaaaag ctaaaaaaga tgatgcccga   120
cagccacttg tgtgaagcat gtgaagccgg tccctccact aagaaaatta gtgaagcatc   180
ttccagtggt ccctccactc acagctcaat cagtgagcaa caggacgaag gaaatgacgt   240
aagccatgac gtctaatccc acaagaattt ccttatataa ggaacacaaa tcagaaggaa   300
gagatcaatc gaaatcaaaa tcggaatcga atcaaaatc ggaatcgaaa tctctcatct   360
ctctctacct tctctctaaa aaacacttag atgtgtgagt aatcacccac ttggggttgt   420
aatatgtagt                                                          430

<210> SEQ ID NO 16
<211> LENGTH: 381
```

-continued

<212> TYPE: DNA (promoter)
<213> ORGANISM: mirabilis mosaic caulimovirus

<400> SEQUENCE: 16
atgttgaaga taagagtggg agccaccact aaaacattgc tttgtcaaaa gctaaaaaag 60
atgatgcccg acagccactt gtgtgaagca tgtgaagccg gtccctccac taagaaaatt 120
agtgaagcat cttccagtgg tccctccact cacagctcaa tcagtgagca acaggacgaa 180
ggaaatgacg taagccatga cgtctaatcc cacaagaatt tccttatata aggaacacaa 240
atcagaagga agagatcaat cgaaatcaaa atcggaatcg aaatcaaaat cggaatcgaa 300
atctctcatc tctctctacc ttctctctaa aaaacactta gatgtgtgag taatcaccca 360
cttggggttg taatatgtag t 381

<210> SEQ ID NO 17
<211> LENGTH: 325
<212> TYPE: DNA (promoter)
<213> ORGANISM: mirabilis mosaic caulimovirus

<400> SEQUENCE: 17
aaagatgatg cccgacagcc acttgtgtga agcatgtgaa gccggtccct ccactaagaa 60
aattagtgaa gcatcttcca gtggtccctc cactcacagc tcaatcagtg agcaacagga 120
cgaaggaaat gacgtaagcc atgacgtcta atcccacaag aatttcctta tataaggaac 180
acaaatcaga aggaagagat caatcgaaat caaaatcgga atcgaaatca aaatcggaat 240
cgaaatctct catctctctc taccttctct ctaaaaaaca cttagatgtg tgagtaatca 300
cccacttggg gttgtaatat gtagt 325

<210> SEQ ID NO 18
<211> LENGTH: 266
<212> TYPE: DNA (promoter)
<213> ORGANISM: mirabilis mosaic caulimovirus

<400> SEQUENCE: 18
aaattagtga agcatcttcc agtggtccct ccactcacag ctcaatcagt gagcaacagg 60
acgaaggaaa tcacgtaagc catgacgtct aatccaacaa gaatttcctt atataaggaa 120
cacaaatcag aaggaagaga tcaatcgaaa tcaaaatcgg aatcgaaatc aaaatcggaa 180
tcgaaatctc tcatctctct ctaccttctc tctaaaaaac acttagatgt gtgagtaatc 240
acccacttgg ggttgtaata tgtagt 266

<210> SEQ ID NO 19
<211> LENGTH: 206
<212> TYPE: DNA (promoter)
<213> ORGANISM: mirabilis mosaic caulimovirus

<400> SEQUENCE: 19
acgaaggaaa tgacgtaagc catgacgtct aatcccacaa gaatttcctt atataaggaa 60
cacaaatcag aaggaagaga tcaatcgaaa tcaaaatcgg aatcgaaatc aaaatcggaa 120
tcgaaatctc tcatctctct ctaccttctc tctaaaaaac acttagatgt gtgagtaatc 180
acccacttgg ggttgtaata tgtagt 206

<210> SEQ ID NO 20
<211> LENGTH: 260
<212> TYPE: DNA (promoter)
<213> ORGANISM: mirabilis mosaic caulimovirus

```
<400> SEQUENCE: 20
ttcgtccaca gacatcaaca tcttatcgtc ctttgaagat aagataataa tgttgaagat        60
aagagtggga gccaccacta aaacattgct ttgtcaaaag ctaaaaaaga tgatgcccga       120
cagccacttg tgtgaagcat gtgaagccgg tccctccact aagaaaatta gtgaagcatc       180
ttccagtggt ccctccactc acagctcaat cagtgagcaa caggacgaag gaaatgacgt       240
aagccatgac gtctaatccc                                                   260

<210> SEQ ID NO 21
<211> LENGTH: 520
<212> TYPE: DNA (promoter)
<213> ORGANISM: mirabilis mosaic caulimovirus

<400> SEQUENCE: 21
tggagattca gaaaaatctc catcaacaaa taatccaagt aaggattaat ggattgatca        60
acatccttac cgctatgggt aagattgatg aaaagtcaaa aacaaaaatc aattatgcac       120
accagcatgt gttgatcacc agctattgtg ggacaccaat ttcgtccaca gacatcaaca       180
tcttatcgtc ctttgaagat aagataataa tgttgaagat aagagtggga gccaccacta       240
aaacattgct ttgtcaaaag ctaaaaaaga tgatgcccga cagccacttg tgtgaagcat       300
gtgaagccgg tccctccact aagaaaatta gtgaagcatc ttccagtggt ccctccactc       360
acagctcaat cagtgagcaa caggacgaag gaaatgacgt aagccatgac gtctaatccc       420
acaagaattt ccttatataa ggaacacaaa tcagaaggaa gagatcaatc gaaatcaaaa       480
tcggaatcga aatcaaaatc ggaatcgaaa tctctcatct                             520

<210> SEQ ID NO 22
<211> LENGTH: 360
<212> TYPE: DNA (promoter)
<213> ORGANISM: mirabilis mosaic caulimovirus

<400> SEQUENCE: 22
ttcgtccaca gacatcaaca tcttatcgtc ctttgaagat aagataataa tgttgaagat        60
aagagtggga gccaccacta aaacattgct ttgtcaaaag ctaaaaaaga tgatgcccga       120
cagccacttg tgtgaagcat gtgaagccgg tccctccact aagaaaatta gtgaagcatc       180
ttccagtggt ccctccactc acagctcaat cagtgagcaa caggacgaag gaaatgacgt       240
aagccatgac gtctaatccc acaagaattt ccttatataa ggaacacaaa tcagaaggaa       300
gagatcaatc gaaatcaaaa tcggaatcga aatcaaaatc ggaatcgaaa tctctcatct       360

<210> SEQ ID NO 23
<211> LENGTH: 311
<212> TYPE: DNA (promoter)
<213> ORGANISM: mirabilis mosaic caulimovirus

<400> SEQUENCE: 23
atgttgaaga taagagtggg agccaccact aaaacattgc tttgtcaaaa gctaaaaaag        60
atgatgcccg acagccactt gtgtgaagca tgtgaagccg gtccctccac taagaaaatt       120
agtgaagcat cttccagtgg tccctccact cacagctcaa tcagtgagca acaggacgaa       180
ggaaatgacg taagccatga cgtctaatcc cacaagaatt tccttatata aggaacacaa       240
atcagaagga gagatcaat cgaaatcaaa atcggaatcg aaatcaaaat cggaatcgaa       300
atctctcatc t                                                            311
```

```
<210> SEQ ID NO 24
<211> LENGTH: 254
<212> TYPE: DNA (promoter)
<213> ORGANISM: mirabilis mosaic caulimovirus

<400> SEQUENCE: 24
aaagatgatg cccgacagcc acttgtgtga agcatgtgaa gccggtccct ccactaagaa      60
aattagtgaa gcatcttcca gtggtccctc cactcacagc tcaatcagtg agcaacagga    120
cgaaggaaat gacgtaagcc atgacgtcta atcccacaag aatttcctta tataaggaac    180
acaaatcaga aggaagagat caatcgaaat caaaatcgga atcgaaatca aaatcggaat    240
cgaaatctct catc                                                      254

<210> SEQ ID NO 25
<211> LENGTH: 297
<212> TYPE: DNA (promoter)
<213> ORGANISM: mirabilis mosaic caulimovirus

<400> SEQUENCE: 25
ttcgtccaca gacatcaaca tcttatcgtc ctttgaagat aagataataa tgttgaagat     60
aagagtggga gccaccacta aaacattgct ttgtcaaaag ctaaaaaaga tgatgcccga    120
cagccacttg tgtgaagcat gtgaagccgg tccctccact aagaaaatta gtgaagcatc    180
ttccagtggt ccctccactc acagctcaat cagtgagcaa caggacgaag gaaatgacgt    240
aagccatgac gtctaatccc acaagaattt ccttatataa ggaacacaaa tcagaag      297

<210> SEQ ID NO 26
<211> LENGTH: 329
<212> TYPE: DNA (promoter)
<213> ORGANISM: mirabilis mosaic caulimovirus

<400> SEQUENCE: 26
ttcgtccaca gacatcaaca tcttatcgtc ctttgaagat aagataataa tgttgaagat     60
aagagtggga gccaccacta aaacattgct ttgtcaaaag ctaaaaaaga tgatgcccga    120
cagccacttg tgtgaagcat gtgaagccgg tccctccact aagaaaatta gtgaagcatc    180
ttccagtggt ccctccactc acagctcaat cagtgagcaa caggacgaag gaaatgacgt    240
aagccatgac gtctaatccc acaagaattt ccttatataa ggaacacaaa tcagaaggaa    300
gagatcaatc gaaatcaaaa tcggaatcg                                     329
```

REFERENCES

An, G., Costa, M. A., Mitra, A., Ha, S-B, Marton, L., Organ-specific and developmental regulation of the nopaline synthase promoter in transgenic tobacco plants, Plant Physiol., 88: 547–552 (1988).

Assaad, F. F., Signer, E. R., Cauliflower mosaic virus P35S promoter activity in *Escherichia coli,* Mol. Gen. Genet., 223: 517–520 (1990).

Ballas, N., Shimshon, B., Hermona, S., Abrahim, L., Efficient functioning of plant promoters and polyadenylated sites in *Xenopus oocytes,* Nucl. Acids Res., 17: 7891–7904 (1989).

Benfey, P. N., Chua, N. H., The cauliflower mosaic virus 35S promoter: combinatorial regulation of transcription in plants, Science 250: 959–966 (1990).

Benfey, P. N., Ren, L., Chua, N. H., Combinatorial and synergistic properties of CaMV 35S enhancer subdomains, EMBO J, 9: 1685–1696 (1990a).

Benfey, P. N., Ren, L., Chua, N. H., Tissue-specific expression from CaMV 35S enhancer subdomains in early stages of plant development, EMBO J, 9: 1677–1684 (1990b).

Benfey, P. N., Ren, L., Chua, N. H., The CaMV 35S enhancer contain at least two domains which can confer different developmental and tissue-specific expression patterns, EMBO J, 8: 2195–2202 (1989).

Berger, P. H., Hunt, A. G., Domier, L. L., Hellmann, G. M., Stram, Y., Thombury, D. W., Pirone, T. P., Expression in transgenic plants of a viral gene product that mediates insect transmission of potyviruses, Proc. Natl. Acad. Sci. (USA) 86: 8402–8406 (1989).

Bhattacharyya-Pakrasi, M., Pen, J., Elmer, J. S., Laco, G., Shen, P., Kaniewska, M. B., Kononowicz, H., Wen, F., Hodges, T. K., Beachy, R. N., Specificity of a promoter from the rice tungro baciliform virus for expression in pholem tissues, Plant J., 4: 71–79 (1993).

Chomczvnski, P., Sacchl, N., Single-step method of RNA isolation by acid guanidinium thiocyanate-phenol-chloroform extraction, Analt. Biochem., 162: 156–159 (1987).

Day Dowson, M. J., Ashurst, J. L., Mathias, S. F., Watts, J. W., Wilson, T. M. A., Dixon, R. A., Plant viral leaders influence expression of a reporter gene in tobacco, Plant Mol. Biol., 23: 97–109 (1993).

Driesen, M., Benito-Moreno, R. M., Hohn, T., Futterer, J., Transcription from the CaMV 19S promoter and autocatalysis of translation from CaMV RNA, Virology, 195: 203–210 (1993).

Fang, R. X., Nagy, F., Sivasubrarnaniarn, S., Chua, N. H., Multiple Cis regulatory elements for maximal expression of the cauliflower mosaic virus 35S promoter in transgenic plants, Plant Cell, 1: 141–150 (1989).

Graybosh, R., Hellmann, G. M., Shaw, J. G., Rhoads, R. E., Hunt, A. G., Expression of a potyvirus nonstructural protein in transgenic tobacco, Biochem. Biophys. Res. Commun., 160: 425–432 (1989).

Guiley, H., Dudley, R. K., Jonard, G., Balasze, E., Richards, K. E., Transcription of cauliflower mosaic virus DNA: detection of promoter sequences and characterization of transcripts, Cell, 30: 763–773 (1982).

Hasegawa, A., Verver, J., Shimada, A., Saito, M., Goldbach, R., van Kammen, A., Miki, K., Kameya-Iwaki, M. and Hibi, T., The complete sequence of soybean chlorotic mottle virus DNA and the identification of a novel promoter, Nucl. Acids Res., 17: 9993–10013 (1989).

Holtorf, S., Apel, K., Bohlmann, H., Comparison of different constitutive and inducible promoters for the over expression of transgenes in Arabidopsis thahana, Plant Mol. Biol., 29: 637–646 (1995).

Hull, R., Covey, S., Replication of cauliflower mosaic virus, Sci. Prog. Oxf., 168, 403–422 (1983).

Jefferson, R. A., Kavanagh, T. A., Bevan, M. W., Gus fusion: β-glucurodinase as a sensitive and versatile gene fusion marker in higher plants, EMBO J, 6: 3901–3907 (1987).

Kay, R., Chan, R., Daly, M., McPherson, J., Duplication of CaMV 35S promoter sequence creates a strong enhancer for plant genes, *Science,* 236, 1299–1302 (1987).

Lam, E., Benfey, P. N., Gilmartin, P. M., Fang, R. X., Chua, N. H., Site specific mutation alter in vitro factor binding and change of promoter expression pattern in plants, Proc. Natl. Acad. Sci USA, 86: 7890–7894 (1989).

Lam, E., Analysis of tissue-specific elements in the CaMV 35S promoter. In Nover, L. ed, *Results and Problems in Cell differentiation, Plant Promoters and transcription factors,* Vol 20, pp 181–196, Springer-Verlag Berlin Heidelberg (1994).

Liod, A. M., Walbot, V., Davis, R. W., Arabidopsis and Nicotiana anthrocyanin production activated by maize regulators R and C1, Science, 258:1773–1775 (1992).

Maiti, I. B., Gowda, S., Kiernan, J., Ghosh, S. K., Shepherd, R. J., Promoter/leader deletion analysis and plant expression vectors with the figwort mosaic virus (FMV) fill length transcript (FLt) promoter containing single and double enhancer domains, Transgenic Research, 6:143–156 (1997).

Maiti, I. B., Hunt, A. G., Developing genetically engineered disease, pest and herbicide resistance in tobacco, Rec. Adv. Tobacco Sci., 18: 45–68 (1992).

Maiti, I. B., Von Lanken, C., Hunt, A. G., Properties of transgenic plants that express a functional potyvirus PI proteinase gene, Personal communication (1995a).

Maiti, I. B., Hunt, A. H., Expression of the tobacco vein mottling virus nuclesr inclusion protein (NIa) gene in tobacco, J. Cell. Biochem. Supplement 16F, Abs. No. Y213 (1992a).

Maiti, I. B., Gowda, S., Kiernan, J., Ghosh, S. K., Shepherd, R. J., Analysis of the figwort mosaic virus (FMV) full length transcript (FLt) promoter: Developing and testing of plant expression vectors with the FMV FLt promoter containing single or double enhancer domains, Proceedings of the International Symposium of Engineering Plants for Commercial Products and Applications (Abstract No. 28), Oct. 1–4, 1995, University of Kentucky, Lexington, Ky., USA.

Maiti, I. B., Hong, Y., Hellnan, G. M., Lanken, C. V., Hunt, A., Multiple potyvirus genes do not confer protection upon plants additively, 4th Congress of ISPMB meeting (abstract), Jun. 19–24, 1994, Amsterdam, The Netherlands.

Maiti, I. B., Hunt, A. G., Wagner, G. J., Seed-transmissible expression of mammalian metallothionein in transgenic tobacco, Biochem. Biophys. Res. Commun., 150: 640–647 (1988).

Maiti, I. B., Murphy, J., Shaw, J. G., Hunt, A. H., Expression of the tobacco vein mottling virus coat protein (CP) and cylinderical inclusion protein (CI) genes in tobacco, 3rd Int. Congress Int. Soc. Plant Mol. Biol., p1154, (1991a).

Maiti, I. B., Wagner, G. J., Hunt, A. G., Light inducible and tissue-specific expression of a chimeric mouse metallothionein cDNA gene in tobacco, Plant Science, 76: 99–107 (1991).

Maiti, I. B., Wagner, G. J., Yeargan, R., Hunt, A. G., Inheritance and expression of the mouse metallothionein gene in tobacco, Plant Physiol., 91: 1021–1024 (1989).

Maiti, I. B., Shepherd, R. J., Isolation and expression analysis of peanut chlorotic streak caulimovirus (PC1SV) full-length transcript (FLt) promoter in transgenic plants, Biochem. Biophys. Res. Commun., 244: 440–444 (1998).

Maiti, I. B., Murphy, J. F., Shaw, J. G., Hunt, A. G., Plant that express a potyvirus proteinase genes are resistant to virus infection, Proc. Natl. Acad. Sci. USA, 90, 6110–6114 (1993).

McNeall, J., Sandey, A., Gray, P. P., Chesterman, C. N., Sleigh, M. J., Hyperinducible gene expression from a metallothionein promoter containing additional metal responsive elements, Gene, 76: 81–88 (1989).

Medberry, S. L., Lockhart, B. E. L., Olszewski, N. E., The Commelina yellow mottle virus promoter is a strong promoter in vascular and reproductive tissues, Plant Cell, 4: 185–192 (1992).

Mitsuhara, I., Ugaki, M., Hirochika, H., Ohshiima, M., Murakami, T., Gotoh, Y., Katayose, Y., Nakamura, S., Honkura, R., Nishimiya, S., Uneo, K., Mochizuki, A., Tanimoto, H., Tsugawa, H., Otsuki, Y., Ohashi, Y., Efficient promoter cassettes for enhanced expression of foreign genes in dicotyledonous and monocotyledonous plants, Plant Cell Physiol., 37: 49–59 (1996).

Odell, J. T., Nagy, F., Chua, N. H., Identification of DNA sequences required for activity of the cauliflower mosaic virus 35S promoter, Nature, 313: 810–812 (1985).

Omirulleh, S., Abraham, M., Golovkin, M., Stefanov, I., Karabaev, M. K., Mustardy, L., Morocz, S., Dudits, D., Activity of a chimeric promoter with the double CaMV 35S enhancer elements in protoplast-derived cells and transgenic plants in maize, Plant Mol. Biol., 21, 415–428 (1993).

Ow, D. W., Jacobs, J. D., Howell, S. H., Functional regions of the cauliflower mosaic virus 35S RNA promoter determined by use of the firely luciferase gene as a reporter of promoter activity, Proc. Nat. Acad. Sci. USA, 84: 4870–4874 (1987).

Pfeiffer, P., Hohn, T., Involvement of reverse transcription in the replication of cauliflower mosaic virus: A detailed model and test of some aspects, Cell, 33, 781–789 (1983).

Pobjecky, N., Rosenberg, G. H., Dinter-Gottlieb, G., Kaufer, N. F., Expression of the β-glucuronidase gene under the control of the CaMV 35S promoter in *Schizosaccharomyces pombe,* Mol Gen. Genet., 220: 314–316 (1990).

Qin, X. F., Holuigue, L., Horvath, D. M., Chua, N. H., Immediate early transcription activation by salicylic acid via the cauliflower mosaic virus as-1 element, The Plant Cell, 6: 863–874 (1994).

Richins, R. D., Shepherd, R. J., Physical maps of the genome of dalilia mosaic virus and mirabilis mosaic virus—two members of the caulimovirus group, Virology, 124: 208–214 (1983)

Sanger, M., Daubert, S., Goodman, R. M., Characteristics of a strong promoter from figwort mosaic virus: comparison with the analogous 35S promoter from cauliflower mosaic virus and the regulated mannopine synthase promoter, Plant Mol. Biol., 14: 433–443 (1990).

Schardl, C. L., Byrd, A. D., Benzion, G., Altschuler, M. A., Hildebrand, D. F., Hunt, A. G., Design and construction of a versatile system for the expression of foreign genes in plants. Gene, 61, 1–11(1987).

Verdaguer, B., de Kochko, A., Beachy, R. N., Fauquet, C., Isolation and expression in transgenic tobacco and rice plants, of the casava vein mosaic virus (CVM) promoter, Plant Mol. Biol., 31: 1129–1139 (1996).

Wagner, G. J., Improving tobacco through metabolic engineering: Promise and obstacles, Rec, Adv. Tobacco. Sci. 18: 3–43 (1992).

Wilmink, A., van de Ven, B. C. E., Dons, J. J. M., Activity of constitutive promoter in various species from the Liliaceae, Plant Mol. Biol., 28: 949–955 (1995).

Yeargan, R., Maiti, I. B., Nielsen, M. T., Hunt, A. G., Wagner, G. J., Tissue partitioning of cadmium in transgenic tobacco seedlings and field grown plants expressing the mouse metallothionein I gene, Transgenic Research, 1: 261–267 (1992).

Yin, Y., Beachy, R., The regulatory region of the rice tungro bacilliform virus promoter and interacting nuclear factor in rice (*Oryza sativa* L.), Plant J, 7: 969–980 (1995).

Zahm, P., Seong-Iyul, R., Klaus, G., Promoter activity and expression of sequences from Ti-plasmid stably maintained in mammalian calls. Mol. Cell Biochem, 90: 9–18 (1989).

What is claimed is:

1. A gene construct comprising an isolated mirabilis mosaic caulimovirus (MMV) full length transcript (FLt) promoter, a 3' untranslated region downstream of the promoter's TATA box, wherein said 3' untranslated region is obtained from a source other than which is found naturally linked to said promoter, and a protein coding sequence.

2. A gene construct comprising in the 5' to 3' direction:
   1) a MMV FLt promoter comprising a single enhancer domain;
   2) a 3' untranslated region downstream of the promoter's TATA box; and
   3) a protein coding sequence.

3. A gene construct comprising in the 5' to 3' direction:
   1) a MMV FLt promoter comprising duplicated enhancer domains;
   2) a 3' untranslated region downstream of the promoter's TATA box; and
   3) a protein coding sequence.

4. An isolated mirabilis mosaic caulimovirus (MMV) FLt promoter, said MMV FLt promoter comprising the sequence identified in SEQ ID NO:1 or a fragment thereof that directs transcription of a down stream gene in plants.

* * * * *